United States Patent
Borkum et al.

(10) Patent No.: US 12,194,307 B2
(45) Date of Patent: *Jan. 14, 2025

(54) **METHODS AND APPARATUSES FOR ACTIVATION OF *ZUSANLI* ST36 ACUPOINT AND OTHER ACUPOINTS BY COMBINED HEATING AND PULSED MAGNETIC ACTIVATION**

(71) Applicants: Jonathan M Borkum, Orono, ME (US); Mohsen Shahinpoor, Kansas City, MO (US); Parsa Shahinpoor, Portland, OR (US)

(72) Inventors: Jonathan M Borkum, Orono, ME (US); Mohsen Shahinpoor, Kansas City, MO (US); Parsa Shahinpoor, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,284

(22) Filed: Mar. 12, 2024

(65) Prior Publication Data
US 2024/0216709 A1    Jul. 4, 2024

Related U.S. Application Data

(63) Continuation-in-part of application No. 18/448,351, filed on Aug. 11, 2023, now Pat. No. 11,964,162, (Continued)

(51) Int. Cl.
*A61N 2/00*    (2006.01)
*A61F 7/00*    (2006.01)
(Continued)

(52) U.S. Cl.
CPC .............. *A61N 2/002* (2013.01); *A61F 7/007* (2013.01); *A61N 2/004* (2013.01); *A61N 2/12* (2013.01); *A61F 2007/008* (2013.01)

(58) Field of Classification Search
CPC .................. A61N 2/002; A61N 5/0625; A61N 2005/0659; A61B 5/316
See application file for complete search history.

(56) References Cited

U.S. PATENT DOCUMENTS

| 4,262,672 A | 4/1981 | Kief |
| 4,269,199 A | 5/1981 | Armitage |

(Continued)

FOREIGN PATENT DOCUMENTS

| CN | 1762509 A | 4/2006 |
| CN | 2863098 Y | 1/2007 |
| CN | 105148398 A | 12/2015 |

OTHER PUBLICATIONS

Lu DP, Lu GP, Gabriel PL. Comparing the clinical effect of five varying locations of LI.4 acupoint. Acupunct Electrother Res. 2008;33(3-4):135-143.
(Continued)

*Primary Examiner* — Carrie R Dorna
*Assistant Examiner* — Joshua Daryl D Lannu
(74) *Attorney, Agent, or Firm* — V Gerald Grafe

(57) ABSTRACT

Systems and devices for continuous heating combined with oscillatory magnetic stimulation of the ST36 acupoint and/or other acupoint(s) by noninvasive heating and transcutaneous magnetic field stimulation, and applied to the treatment of several physical conditions.

20 Claims, 18 Drawing Sheets

Related U.S. Application Data which is a continuation-in-part of application No. 18/068,648, filed on Dec. 20, 2022.

(51) Int. Cl.
*A61N 2/02* (2006.01)
*A61N 2/12* (2006.01)
*A61N 5/06* (2006.01)

(56) References Cited

U.S. PATENT DOCUMENTS

| | | | |
|---|---|---|---|
| 4,341,227 | A | 7/1982 | Turner |
| 4,448,198 | A | 5/1984 | Turner |
| 4,535,784 | A | 8/1985 | Rohlicek |
| 4,553,546 | A | 11/1985 | Javelle |
| 4,621,642 | A | 11/1986 | Chen |
| 4,633,875 | A | 1/1987 | Turner |
| 5,010,897 | A | 4/1991 | Leveen |
| 6,347,251 | B1 | 2/2002 | Deng |
| 8,380,298 | B2 | 2/2013 | Chi |
| 8,382,834 | B2 | 2/2013 | Prescott |
| 8,805,512 | B1 | 8/2014 | Greiner |
| 8,932,198 | B1 | 1/2015 | You |
| 8,996,125 | B2 | 3/2015 | Greiner |
| 9,061,135 | B1 | 6/2015 | Keller |
| 9,233,258 | B2 | 1/2016 | Simon |
| 9,327,134 | B2 | 5/2016 | Greiner |
| 9,364,390 | B2 | 6/2016 | Greiner |
| 9,403,001 | B2 | 8/2016 | Simon |
| 9,433,786 | B2 | 9/2016 | Greiner |
| 9,452,104 | B2 | 9/2016 | Greiner |
| 9,549,872 | B2 | 1/2017 | Chen |
| 9,566,212 | B2 | 2/2017 | Greiner |
| 9,724,512 | B2 | 8/2017 | Peterson |
| 10,207,106 | B2 | 2/2019 | Simon |
| 10,512,769 | B2 | 12/2019 | Simon |
| 10,518,082 | B2 | 12/2019 | Greiner |
| 10,933,251 | B1 | 3/2021 | Borkum |
| 10,940,033 | B2 | 3/2021 | Greiner |
| 11,266,850 | B2 | 3/2022 | Prouza |
| 11,344,738 | B2 | 5/2022 | Marcantonio |
| 2013/0131753 | A1 | 5/2013 | Simon |
| 2014/0051906 | A1 | 2/2014 | Chen |
| 2020/0101307 | A1* | 4/2020 | Marcantonio ......... A61H 39/08 |
| 2021/0379374 | A1 | 12/2021 | Hamner |
| 2022/0323784 | A1 | 10/2022 | Cassano |
| 2023/0173278 | A1 | 6/2023 | Wang |

OTHER PUBLICATIONS

Nam MH, Yin CS, Soh KS, Choi SH. Adult neurogenesis and acupuncture stimulation at ST36. J Acupunct Meridian Stud. 2011;4(3):153-158.

Niu X, Wen Z, Li X, Zhao W, Li X, Huang Y, et al. Fabrication of graphene and gold nanoparticle modified acupuncture needle electrode and its application in rutin analysis, Sensors and Actuators B: Chemical, 2018;255 Part 1:471-477.

GBD 2016 Dementia Collaborators. Global, regional, and national burden of Alzheimer's disease and other dementias, 1990-2016: a systematic analysis for the Global Burden of Disease Study 2016. Lancet Neurol. 2019;18:88-106.

Bherer L, Erickson KI, Liu-Ambrose T. A review of the effects of physical activity and exercise on cognitive and brain functions in older adults. Journal of Aging Research. 2013:657508.

Blondell SJ, Hammersley-Mather R, Lennert Veerman J. Does physical activity prevent cognitive decline and dementia? A systematic review and meta-analysis of longitudinal studies. BMC Public Health. 2014;14:510.

Heyn P, Abreu BC, Ottenbacher KJ. The effects of exercise training on elderly persons with cognitive impairment and dementia: a meta-analysis. Arch Phys Med Rehabil. 2004;85:1694-1704.

Wang R, Holsinger RMD. Exercise-induced brain-derived neurotrophic factor expression: Therapeutic implications for Alzheimer's dementia. Ageing Research Reviews. 2018;48:109-121.

Trigiani LJ, Hamel E. An endothelial link between the benefits of physical exercise and dementia. Journal of Cerebral Blood Flow and Metabolism. 2017;37:2649-2664.

Kim S-E, Ko I-G, Kim B-K, et al. Treadmill exercise prevents aging-induced failure of memory through an increase in neurogenesis and suppression of apoptosis in rat hippocampus. Experimental Gerontology. 2010;45:357-365.

Erickson KI, Voss MW, Shaurya Prakash R, et al. Exercise training increases size of hippocampus and improves memory. PNAS. 2011;108:3017-3022.

Greenberg PE, Fournier A-A, Sisitsky T, Pike CT, Kessler RC. The economic burden of adults with Major Depressive Disorder in the United States (2005 and 2010). J Clin Psychiatry. 2015;76:155-162.

Laursen TM, Musliner KL, Benros ME, Vestergaard M, Munk-Olsen T. Mortality and life expectancy in persons with severe unipolar depression. J Affect Disord. 2016;193:203-207.

Global Burden of Disease Study 2013 Colllaborators. Global, regional, and national incidence, prevalence, and years lived with disability for 301 acute and chronic diseases and injuries in 188 countries, 1990-2013: A systematic analysis for the Global Burden of Disease Study 2013. Lancet. 2015;386:743-800.

Morres ID, Hatzigeorgiadis A, Stathi A, Comoutos N, Arpin-Cribbie C, Krommidas C, Theodorakis Y. Aerobic exercise for adult patients with major depressive disorder in mental health services: a systematic review and meta-analysis. Depress Anxiety. 2019;36:39-53.

Belvederi Murri M, Ekkekakis P, Magagnoli M, Zampogna D, Cattedra S, Capobianco L, et al. Physical exercise in major depression: reducing the mortality gap while improving clinical outcomes. Frontiers in Psychiatry. 2019;9:762.

Tobi P, Kemp P, Schmidt E. Cohort differences in exercise adherence among primary care patients referred for mental health versus physical health conditions. Primary Health Care Research and Development. 2017;18:463-471.

Li P, Tjen-A-Looi SC, Cheng L, Liu D, Painovich J, Vinjamury S, Longhurst JC. Long-lasting reduction of blood pressure by electroacupuncture in patients with hypertension: randomized controlled trial. Med Acupunct. 2015;27:253-265.

Wu, W-Y., Chen, W-H, Hsieh C-L, Lin Y-W. Abundant expression and functional participation of TRPV1 at Zusanli acupoint (ST36) in mice: mechanosensitive TRPV1 as an "acupuncture responding channel." BMC Complement Altern Med. 2014;14:96.

Caterina, M. J. et al. The capsaicin receptor: a heat-activated ion channel in the pain pathway. Nature. 1997;389:816-824.

Wu Y-Y, Jiang Y-L, He X-F, Zhao X-Y, Shao X-M, Sun J, Shen Z, Shou S-Y, Wei J-J, Ye J-Y, Yan S-S, Fang J-Q. 5-HT in the dorsal raphe nucleus is involved in the effects of 100-Hz electroacupuncture on the pain-depression dyad in rats. Exp Ther Med. 2017;14:107-114.

Tao J, Chen B, Gao Y, Yang S, Huang J, Jiang X, Wu Y, Peng J, Hong Z, Chen L. Electroacupuncture enhances hippocampal NSCs proliferation in cerebral ischemia-reperfusion injured rats via activation of notch signaling pathway. Int J Neurosci. 2014;124:204-212.

Chavez LM, Huang S-S, MacDonald I, Lin J-G, Lee Y-C, Chen Y-H. Mechanisms of acupuncture therapy in ischemic stroke rehabilitation: a literature review of basic studies. Int J Mol Sci. 2017;18:2270.

Leung SB, Zhang H, Lau CW, Lin Z-X. Attenuation of blood pressure in spontaneously hypertensive rats by acupuncture was associated with reduction in oxidative stress and improvement from endothelial dysfunction. Chin Med. 2016;11:38.

Lee CH, Kim D-K, Yook T-H, Sasaki M, Kitamura N. Effectiveness of electroacupuncture at Zusanli (ST36) on the immunohistochemical density of enteroendocrine cells related to gastrointestinal function. J Acupunct Meridian Stud. 2012;5:63-71.

Yu C-C, Ma C-Y, Wang H, King L-H, Zhao Y, Shen F, Wu M. Effects of acupuncture on Alzheimer's disease: evidence from neuroimaging studies. Chin J Integr Med. 2018. DOI: 10.1007/s11655-018-2993-3.

Nam M-H, Ahn KS, Choi S-H. Acupuncture stimulation induces neurogenesis in adult brain. Int Rev Neurobiol. 2013;111:67-90.

(56) References Cited

OTHER PUBLICATIONS

Tong T, Pei C, Chen J, Lv Q, Zhang F, Chen g Z. Efficacy of acupuncture therapy for chemotherapy-related cognitive impairment in breast cancer patients. Med Sci Monit. 2018;24:2919-2927.

Zhang Q, Li Y-N, Guo Y-Y, Yin C=P, Gao F, Xin X, Huo S-P, Wang X-L, Wang Q-J. Effects of preconditioning of electro-acupuncture on postoperative cognitive dysfunction in elderly: A prospective, randomized, controlled trial. Medicine. 2017;96:26(e7375).

Huang L-P, Zhou S, Lu Z, Tian Q, Li X, Cao L-J, Yu J-h, Wang H. Bilateral effect of unilateral electroacupuncture on muscle strength. J Altern Complement Med. 2007;13:539-546.

Le J-J, Yi T, Qi L, Li J, Shao L, Dong J-C. Electroacupuncture regulate hypothalamic-pituitary-adrenal axis and enhance hippocampal serotonin system in a rat model of depression. Neuroscience Letters. 2016;615:66-71.

Sun H, Zhao H, Ma C, Bao F, Zhang J, Wang D-H, et al. Effects of electroacupuncture on depression and the production of glial cell line-derived neurotrophic factor compared with fluoxetine: a randomized controlled pilot study. Journal of Alternative and Complementary Medicine. 2013;19:733-739.

Wang H, Yang G, Wang S, Zheng X, Zhang W, Li Y. The most commonly treated acupuncture indications in the United States: a cross-sectional study. American Journal of Chinese Medicine. 2018;46:1387-1419.

Smith CA, Armour M, Lee MS, Wang LQ, Hay PJ. Acupuncture for depression. Cochrane Database Syst Rev. 2018;3:CD004046.

Youn J-I, Sung K-K, Song B-K, Kim M, Lee S. Effects of electroacupuncture therapy on post-stroke depression in patients with different degrees of motor function impairments: a pilot study. J Phys Ther Sci. 2013;25:725-728.

Li XB, Wang J, Xu AD, Huang JM, Meng LQ, Huang RY, Xu J. Clinical effects and safety of electroacupuncture for the treatment of post-stroke depression: a systematic review and meta-analysis of randomised controlled trials. Acupunct Med. 2018;36:284-293.

Simonsen EB. Contributions to the understanding of gait control. Dan Med J. 2011;61(4):B4823.

Ruiz-Muñoz M, Cuesta-Vargas AI. Electromyography and sonomyography analysis of the tibialis anterior: a cross sectional study. J Foot Ankle Res. 2014;7:11.

Scott LA, Murley GS, Wickham JB. The influence of footwear on the electromyographic activity of selected lower limb muscles during walking. J Electromyogr Kinesiol. 2012;22:1010-1016.

Shelburne KB, Torry MR, Pandy MG. Muscle, ligament, and joint-contact forces at the knee during walking. Med Sci Sports Exerc. 2005;37:1948-1956.

Chapple W. Proposed catalog of the neuroanatomy and the stratified anatomy for the 361 acupuncture points of 14 channels. J Acupunct Meridian Stud. 2013;6:270-274.

Deadman P, Al-Khafaji M, Kevin Baker K. Manual of acupuncture. Hove, East Sussex, England: Journal of Chinese Medicine Publications; 2007. (book cited as background information, copy not attached).

Firth J, Firth JA, Stubbs B, Vancampfort D, Schuch FitBit, Hallgren M, et al. Association between muscular strength and cognition in people with major depression and bipolar disorder and healthy controls. JAMA Psychiatry. 2018;75:740-746.

Veronese N, Stubbs B, Trevisan C, Bolzetta F, Rui MD, Solmi M, et al. What physical performance measures predict incident cognitive decline among intact older adults? A 4.4-year follow-up study. Exp Gerontol. 2016;80:110-118.

Fukumori N, Yamamoto Y, Takegami M, Yamazaki S, Onishi Y, Sekiguchi M, Fukuhara S. Association between hand-grip strength and depressive symptoms: Locomotive Syndrome and Health Outcomes in Aizu Cohort Study (LOHAS). Age Ageing. 2015;44:592-598.

Abraham TS, Chen M-L, Ma S-X. TRPV1 expression in acupuncture points: response to electroacupuncture stimulation. J Chem Neuroanat. 2011;41:129-136.

Kawakita K, Shinbara H, Imai K, Fukuda F, Yano T, Kuriyama K. How do acupuncture and moxibustion act? Focusing on the progress in Japanese acupuncture research. J Pharmacol Sci. 2006;100:443-459.

Caterina MJ, Rosen TA, Tominaga M, Brake AJ, Julius D. A capsaicin-receptor homologue with a high threshold for noxious heat. Nature. 1999;398:436-441.

Dewhirst MW, Viglianti BL, Lora-Michiels M, Hanson M, Hoopes PJ. Basic principles of thermal dosimetry and thermal thresholds for tissue damage from hyperthermia. Int J Hyperthermia. 2003;19:267-294.

Edwards RR, Fillingim RB. Effects of Age on Temporal Summation and Habituation of Thermal Pain: Clinical Relevance in Healthy Older and Younger Adults. J Pain. 2001;2:307-317.

Lee I-S, Lee Y-S, Park H-J, Lee H, Chae Y. Evaluation of phantom-based education system for acupuncture manipulation. PLoS One. 2015;10(2):e0117992.

Tan TT, Wang D, Huang JK, Zhou XM, Yuan X, Liang JP, et al. Modulatory effects of acupuncture on brain networks in mild cognitive impairment patients. Neural Regen Res. 2017;12:250-258.

Nishiwaki M, Takayama M, Yajima H, Nasu M, Park J, Kung J, Takakura N. A double-blind study on acupuncture sensations with Japanese style of acupuncture: comparison between penetrating and placebo needles. Evid Based Complement Alternat Med. 2018:8128147.

Yoo S-S, Lee W, Kim H. Pulsed application of focused ultrasound to the LI4 Elicits deqi sensations: pilot study. Complement Ther Med. 2014;22:592-600.

\* cited by examiner

Solenoid magnetic plunger movement towards or away from the ST36 Acupoint

METHODS AND APPARATUSES FOR ACTIVATION OF *ZUSANLI* ST36 ACUPOINT AND OTHER ACUPOINTS BY COMBINED HEATING AND PULSED MAGNETIC ACTIVATION

TECHNICAL FIELD

The present invention is in the field of medical implants and acupuncture. It is broadly related to non-invasive heating and magnetic activation of acupoints used in contact with mammalian skin, over acupoints of interest in a mammalian body, and methods of stimulating the acupoints of interest. More particularly, this invention relates to using a device with a magnetic plunger to magnetically activate certain acupoints whose temperature has been raised to between 44 and 52 degrees C. or so by noninvasive heating of acupoints of interest.

BACKGROUND

Various references are cited in the various parts of this application to facilitate understanding of the present invention. Each such reference is incorporated by reference herein.

In U.S. Pat. No. 10,933,251 a pulsed magnetic field is used to inductively heat ST36 and similar acupoint regions of interest. U.S. Pat. No. 10,933,251's pulsed magnetic induction heating is too inefficient to sufficiently activate the ST36 acupoint without utilizing invasive techniques, such as the implantation of ferromagnetic particles.

In U.S. Pat. No. 8,380,298 B2, acupuncture needles are magnetized through connection to a permanent magnet prior to insertion. The device is proposed as a treatment for weight loss, addictions, and other unspecified ailments. The magnetic field is stationary and is not designed to induce currents through the acupoint. The method is invasive.

In U.S. Pat. No. 11,344,738 B2, acupuncture needles are configured as electromagnets to deliver continuous or varying magnetic fields. Pairs of needles are used with opposing polarities. Magnetic stimulation is not combined with heat, the method is invasive, and the device is not described to treat or prevent cognitive impairment or depression.

In U.S. Pat. No. 11,266,850 B2, flat circular coils are used to noninvasively deliver time-varying magnetic fields to bodily structures to enhance visual appearance through muscle contraction, lysis of adipose tissue, stimulation of collagen production, or to produce analgesia by stimulating nerves. U.S. Pat. No. 11,266,850 B2 describes but does not claim simultaneous use of radiofrequency or optical stimulation to heat the tissue prior to magnetic stimulation. The device is not described for stimulation of acupuncture points, or for treatment or prevention of cognitive impairment or depression.

In U.S. Pat. No. 9,233,258 B2, magnetic fields are used to noninvasively stimulate nerves for the treatment of medical conditions. The device is not described as stimulating acupuncture points and the magnetic stimulation is not combined with heat.

U.S. Pat. No. 10,512,769 B2 comprises transcutaneous magnetic stimulation of the vagus nerve to treat autism spectrum disorder or other behavioral disorder. Similarly, U.S. Pat. No. 9,403,001 B2 includes the use of externally applied magnetic fields to noninvasively modulate activity in a cervical branch of the vagus nerve to treat functional gastrointestinal disorders. In both cases, the role of the magnetic field is to directly modulate the electrical functioning of the nerve. Heat and acupuncture points are not involved, and the device is not designed to prevent or treat cognitive impairment or depression.

U.S. Pat. No. 9,566,212 B2 describes an implantable electroacupuncture device for treating dyslipidemia or obesity, in part by stimulating ST36. Other patents for similar devices are U.S. Pat. No. 9,364,390 B2 for treating obesity, U.S. Pat. No. 9,452,104 B2 for treating cardiovascular disease, U.S. Pat. No. 10,518,082 B2 for treating hypertension, U.S. Pat. No. 9,433,786 B2 for treating Parkinson's disease, U.S. Pat. No. 9,724,512 B2 for treating Parkinson's disease or essential tremor, U.S. Pat. No. 10,940,033 B2 for treating erectile dysfunction, and U.S. Pat. No. 9,327,134 B2 for treating unspecified disorders. The device uses an external magnetic field to control the implanted unit. The device is invasive, does not use heat or magnetic stimulation of the acupoint, and is not intended to treat or prevent cognitive impairment or depression.

U.S. Pat. No. 10,207,106 B2 describes a device that noninvasively electrically stimulates a peripheral nerve, principally the vagus nerve, to treat gastroparesis and functional gastrointestinal disorders. The device is not directed to ST36 or other acupoints, does not use heat or magnetic stimulation, and is not described as treating or preventing a neurodegenerative disease or depression.

Patent application number US 20210379374 A1 describes a device for delivering transcutaneous electrical peripheral nerve stimulation to alter dysfunctional thalamocortical EEG rhythms to treat migraine and other headache conditions. The device does not use heat or magnetic stimulation, is not described as treating or preventing cognitive impairment or depression, and it specifically excludes stimulation of ST36.

Patent number WO 2017107878 A1 describes a device for noninvasive warming of ST36 for unspecified purposes. The device does not use electricity or magnetic stimulation, and is not described as treating or preventing cognitive impairment or depression.

There are several Korean patents in the field. Korean patent numbers KR 20,050,080,004 A and KR 100,686,253 B1 describe devices in which an acupuncture needle is heated through an externally applied magnetic field. The device is invasive and the magnetic field is not configured to induce ion flow in the acupoint.

Korean patent number KR 101,249,387 B1 describes a needle-type electromagnetic device that combines heating and magnetic stimulation of an acupoint. The device is invasive and is not focused on ST36 or on prevention or treatment of cognitive impairment or depression.

The device in Korean patent number KR 100,933,463 B1 consists of an electric coil around a heating core, in which the magnetic field is used to heat the core and therefore noninvasively heat the acupoint. The device is not focused on ST36 or the prevention or treatment of cognitive impairment or depression, and the magnetic field is not configured to induce ion currents in the acupoint.

In addition, Chinese patent number CN 1,037,578 C describes magnetic heating to stimulate acupoints in the sole of the foot to improve blood circulation and general health. No attempt is made to stimulate ST36 or to prevent or treat cognitive impairment or depression.

There are a number of scientific papers addressing ST36 acupuncture point stimulation towards ameliorating cognitive impairment arising from neurodegenerative diseases such as Alzheimer's disease, traumatic brain injury, and stroke, and for preventing age-related cognitive decline. Please refer to the article by Min-Ho Nam, Chang ShikYin, Kwang-SupSoh and Seung-hoon Choi, entitled "Adult Neurogenesis and Acupuncture Stimulation at ST36", Journal of Acupuncture and Meridian Studies, Volume 4, Issue 3, September 2011, Pages 153-158, for a good review of the science. Nam M H, Yin C S, Soh K S, Choi S H. Adult neurogenesis and acupuncture stimulation at ST36. J Acupunct Meridian Stud. 2011; 4(3):153-158.

There are several patents for devices providing steady heat to acupoints. U.S. Pat. No. 8,932,198 B1 describes the use of a steady stream of water vapor, heated to between 38 and 50° C., to steadily warm certain acupuncture points to treat sleep disorders. There are also several U.S. patents and Chinese patents describing acupuncture devices that heat an acupuncture point, invasively or noninvasively, using microwave radiation. For example, U.S. Pat. No. 4,621,642 consists of a central metal bar that functions as a microwave antenna and a surrounding shield, insulated from the antenna. The apparatus, connected to a microwave generator, is placed in contact with the skin above an acupuncture point to heat it. In U.S. Pat. No. 6,347,251 B1, an acupuncture needle, which is the microwave antenna, is surrounded by a circular array of needles. The entire apparatus is inserted into an acupuncture point. The device is invasive and is not configured to magnetically activate the acupoint. No specific applications for the acupuncture are designated.

U.S. Pat. No. 4,262,672 describes an acupuncture needle and surrounding conductor to electrically stimulate acupuncture points to achieve an analgesic effect. The authors note that if a soft ferrite tip were placed in the primary winding it would heat up, thermally stimulating the acupuncture point. Chinese Patent CN 2863098Y describes acupuncture needles with electrothermal properties to heat acupuncture points. In neither case is magnetic induction used to activate the acupoint. The device is also not described as treating or preventing cognitive impairment or depression.

U.S. Pat. No. 9,549,872 issued to Chen, et. al. on January 2017, entitled "Chronic electroaccupuncture [sic] using implanted electrodes" discusses certain embodiments which are directed to methods of treating diabetes, obesity, eating disorders, and gastrointestinal problems using chronically or permanently fully implanted electrodes. In certain aspects a stimulation lead is implanted proximally to an acupoint in the stomach (ST) meridian, which may include ST36, the stimulation lead being coupled to an implantable signal generator; and stimulating the acupoints using the signal generator to treat the metabolic disease. Although the primary intent is electro-acupuncture, the claims include magnetic or microwave stimulation of the electrodes to heat them, thermally stimulating the surrounding tissue. The heat would apparently be steady, be by means of chronically or permanently implanted electrodes and, again, the device is for treating eating disorders, gastrointestinal problems, and metabolic diseases such as diabetes and obesity. Magnetic stimulation of the acupoint itself is not used.

A number of Chinese and Korean patents, and a few U.S. patents, use LEDs to deliver steady or pulsed infrared light to acupuncture points. For example, U.S. Pat. No. 4,553,546 (issued Nov. 19, 1985) uses an 860 nm diode, with a pulse repetition interval of 1.720 or 0.860 msec., placed on the skin above an acupuncture point, to stimulate it. U.S. Pat. No. 4,535,784 (issued Aug. 20, 1985) describes placing LEDs on the skin above an acupuncture point to irradiate it with visible or infrared light. U.S. Pat. No. 9,061,135 B1 (granted Jun. 23, 2015) describes a similar device for treating chronic pain. These patents do not utilize magnetic stimulation of the acupuncture points, nor do they claim the treatment or prevention of cognitive impairment, brain injury, or depression.

United States U.S. Pat. No. 8,996,125 B2 describes a self-contained implanted system for electrical stimulation of certain acupuncture points to treat cardiovascular disease. A second United States patent was subsequently issued for this device, for treating hypertension (U.S. Pat. No. 8,805,512 B1). The device allows for an external electromagnetic field as a remote control for adjusting the stimulation parameters generated by the implanted device. The stimulation used in this device is purely electric. Neither magnetic nor thermal stimulation is employed. An international patent application was filed for essentially the same device (number PCT/US20 Ser. No. 14/024,430, filed Mar. 12, 2013 in the U.S. and Mar. 12, 2014 internationally).

There are also a number of Chinese patents addressing the same. The Chinese Patent CN 105,148,398 A is entitled "Electroacupuncture needle therapeutic instrument for treating brain-derived diseases." This invention "relates to an electroacupuncture needle therapeutic instrument for treating brain-derived diseases and belongs to the medical apparatus and instrument field. With the electroacupuncture needle therapeutic instrument of the invention adopted, a plurality of acupuncture points can be treated simultaneously, the burden of the head of a patient can be decreased, and an excellent stimulating effect can be realized. According to the therapeutic instrument of the invention, an insulating elastic hat is provided with fixing belts which are used for fixing the insulating elastic hat on the head of the patient. The insulating elastic hat is divided into nine regions according to the parietal region, the pre-parietal region, the frontal area, the occipital region, the suboccipital region, the temporal region, the nuchal region, the prefrontal region and the post-parietal region of scalp points. Electroacupuncture needles are arranged in each region of the insulating elastic hat. The electroacupuncture needles are circular-ring-shaped electrodes. The inner round rings of electroacupuncture needle are filled with an electric conduction paste so that the circular-ring-shaped electrodes can act on the acupuncture points of the head of the patient after pulse current passes through the circular-ring-shaped electrodes. The electroacupuncture needle fixing rings penetrate the insulating elastic hat; and the sides of the electroacupuncture needle fixing rings, which are filled with the electric conduction paste, are located at the inner surface of the insulating elastic hat." Neither heating nor magnetic induction are used and the acupuncture points are restricted to those found on the head.

Chinese Patent CN 1,762,509 A presents an electrical pulse generator to electrically stimulate acupuncture points ST36 and LI4 at 2-100 Hz, and at 2 Hz and 100 Hz alternately, in order to improve brain function.

Several patents relate to heating regions of the body to enhance blood flow, to restore temperature after hypothermic surgery or, especially, to selectively destroy tumors or other lesions. U.S. Pat. Nos. 4,341,227 and 4,633,875 describe systems for using electromagnetic radiation in the range of 900 MHZ, from an applicator in contact with the body, to heat the underlying tissue. A sensor inserted into the tissue provides feedback for maintaining constant temperature. In U.S. Pat. No. 4,448,198, electromagnetic radiation is delivered selectively to a tissue at desired depth by using multiple applicators inserted into the body. Constructive interference of the emitted radiation is used to heat the tissue in order to selectively kill tumor cells.

In U.S. Pat. No. 4,269,199, an induction coil is positioned over the body for localized heating of a tumor. In U.S. Pat.

No. 5,010,897, two induction coils are used, one on the anterior surface and one on the posterior surface of the body, heating the area between them by means of magnetic fields whose lines of force pass through the body.

There are also some patents related to internally heating medical implants by magnetic induction which are, however, unrelated to the present invention. U.S. Pat. No. 8,382,834 issued to Prescott on February 2013, entitled "Induction heater system for shape memory medical implants and method of activating shape memory medical implants within the mammalian body" presents a method of altering a medical implant having a shape memory portion. The device includes the use of a probe having a tip provided with an induction coil. The induction coil is electrically coupled to an induction power supply. The induction coil is inserted into the mammalian body. The power supply is activated at a suitable frequency to cause the induction coil to generate a magnetic field, wherein such magnetic field induces eddy currents in the shape memory portion of the implant which are sufficient to heat the shape memory portion of the implant to a phase transformation temperature to effect shape change of the implant.

The prior art is absent any teaching of combined noninvasive heating to open TRPV1 ion channels and pulsed magnetic induction to move ions through the open channels of Zusanli ST36 and other acupoints.

SUMMARY OF INVENTION

Systems and devices for continuous heating combined with oscillatory magnetic stimulation of the ST36 acupoint and/or other acupoint(s) by noninvasive heating and transcutaneous magnetic field stimulation towards (1) ameliorating cognitive impairment arising, for example, from head-injury, stroke, post-Covid-19 syndrome, post-ICU syndrome, and post-chemotherapy for cancer, and neurodegenerative diseases such as Alzheimer's; (2) helping to prevent cognitive impairment from these causes; (3) preventing and treating age-related cognitive decline; and (4) preventing and treating depression manifesting, for example, as Major Depressive Disorder, Dysthymic Disorder, or Adjustment Disorder with Depressed Mood.

The heating system can comprise a noninvasive heating element to continuously heat the ST36 and/or other acupoint(s) to a temperature between 44 and 52 degrees C. The magnetic system comprises a magnetic plunger mounted with an apparatus that positions the plunger near the desired acupoint and provides for motion of the plunger toward and away from the acupoint; motion of the plunger causes the magnetic field experienced by the acupoint to vary with a field strength 0.1-3.0 Tesla and frequency between 0.01-100.0 Hz frequency. The acupoints can be assumed to be circular of 2-4 mm in diameter. Lu D P, Lu G P, Gabriel P L. Comparing the clinical effect of five varying locations of LI.4 acupoint. Acupunct Electrother Res. 2008; 33 (3-4):135-143.

The heating system can comprise a noninvasive heating element in the form of a radially distributed array of LEDs to heat the ST36 and/or other acupoint(s) to temperatures between 44 and 52 degrees C. to open the TRPV1 ion channels. There can be more radially distributed noninvasive heating cells closer to the ST36 acupoint. Thus due to a higher population density of LED's near the acupoint ST36 and heating power closer to the ST36 acupoint will heat it up quicker and faster. The magnetic stimulation system comprises a magnetic plunger, e.g., a stack of neodymium disk-shaped magnets; stacked to produce a magnetic field with field strength of 0.1 to 3.0 Tesla, and mounted with a control, e.g., a solenoid, to translate the plunger relative to the acupoint such that the magnetic field from the plunger experienced by the acupoint varies at from 0.01 to 100.0 Hz frequency to induce movement of ions through the open TRPV1 channels. The magnetic stimulation can optimized for movement of ions through the acupoint and does not in and of itself heat the acupoint (i.e., there is no magnetic induction heating). The acupoints can be assumed to be circular of 2-4 mm in diameter. The electrical lead connections, battery, noninvasive heating element, and magnetic plunger can be embedded in a brace (distal to the knee in the case of the ST36 acupoint) to be in contact with the skin over the acupoint region (see FIGS. 1, 2 and 3).

The invention described here is based on the discovery that the anatomical basis of the ST36 acupoint involves TRPV1 ion channels. The heating element is designed to shift the TRPV1 ion channels in the acupoint to an open configuration so that they can be activated by inflow of calcium ions. The magnetic plunger is designed to generate a magnetic field to induce movement of ions through the acupoint's ion channels through magnetic induction, in order to activate the acupoint. This mechanism is based on the anatomical understanding of the acupoint, which makes it possible to activate the acupoint noninvasively and without potentially harmful levels of heat. Our mechanism is thus distinct and superior to traditional acupuncture and moxibustion, which are invasive and can be associated with injurious heat exposure respectively. Electrical lead connections, battery, the noninvasive heating element, and the magnetic plunger can be embedded in a brace close to and almost in contact with the skin over the acupoint region (under the knee in the case of the ST36 acupoint).

DESCRIPTION OF THE INVENTION

Figure 1:
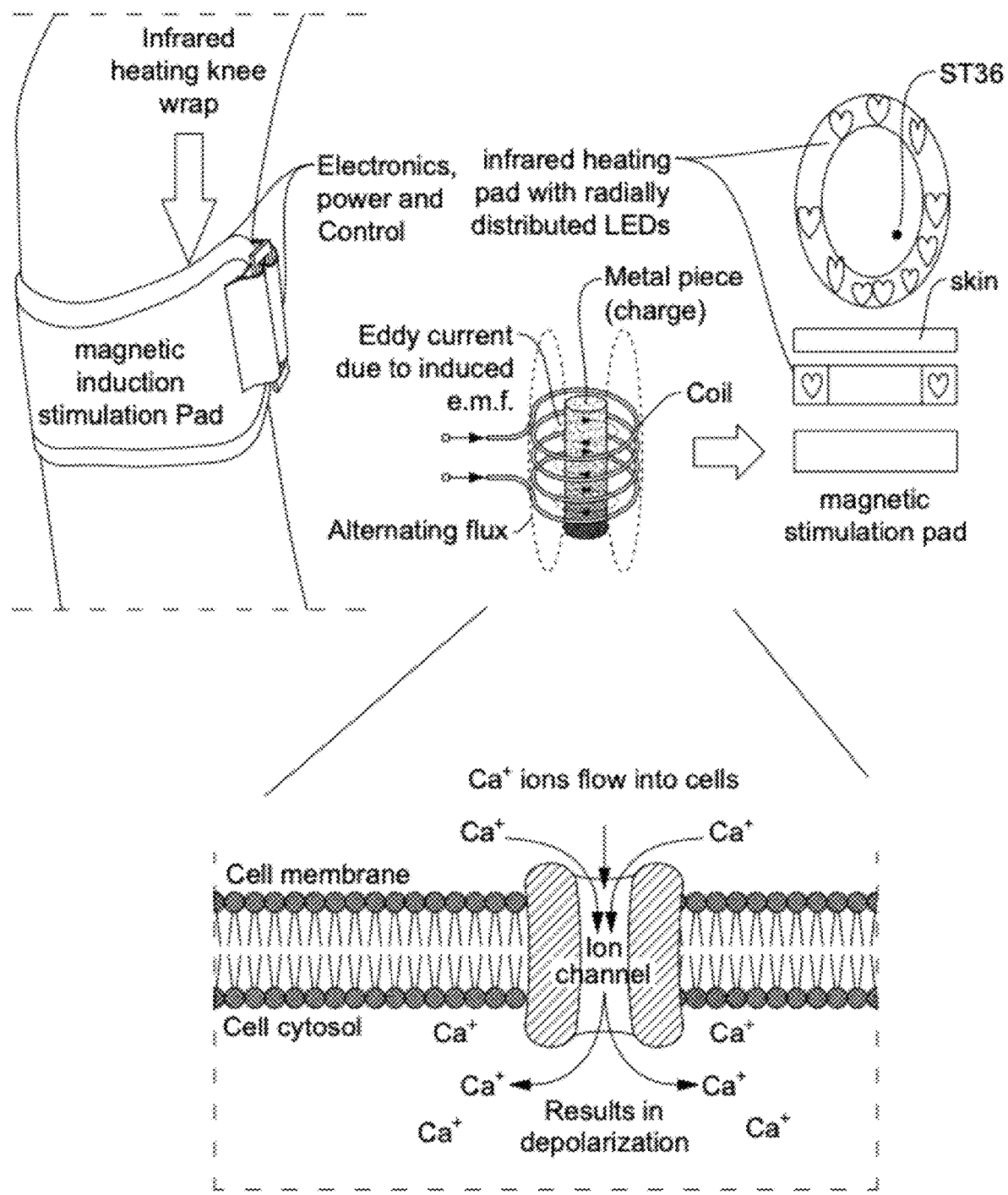
FIG. 1 is a schematic illustration of an arrangement of magnetic stimulation and noninvasive heating kneepads.

FIG. 1 illustrates a general arrangement of magnetic stimulation and noninvasive heating kneepads in an example embodiment. Note the higher population density of noninvasive heating elements close to ST36 Acupoint. The magnetic induction coil moves calcium ions through the open TRPV1 channels in the acupoint.

Figure 2:
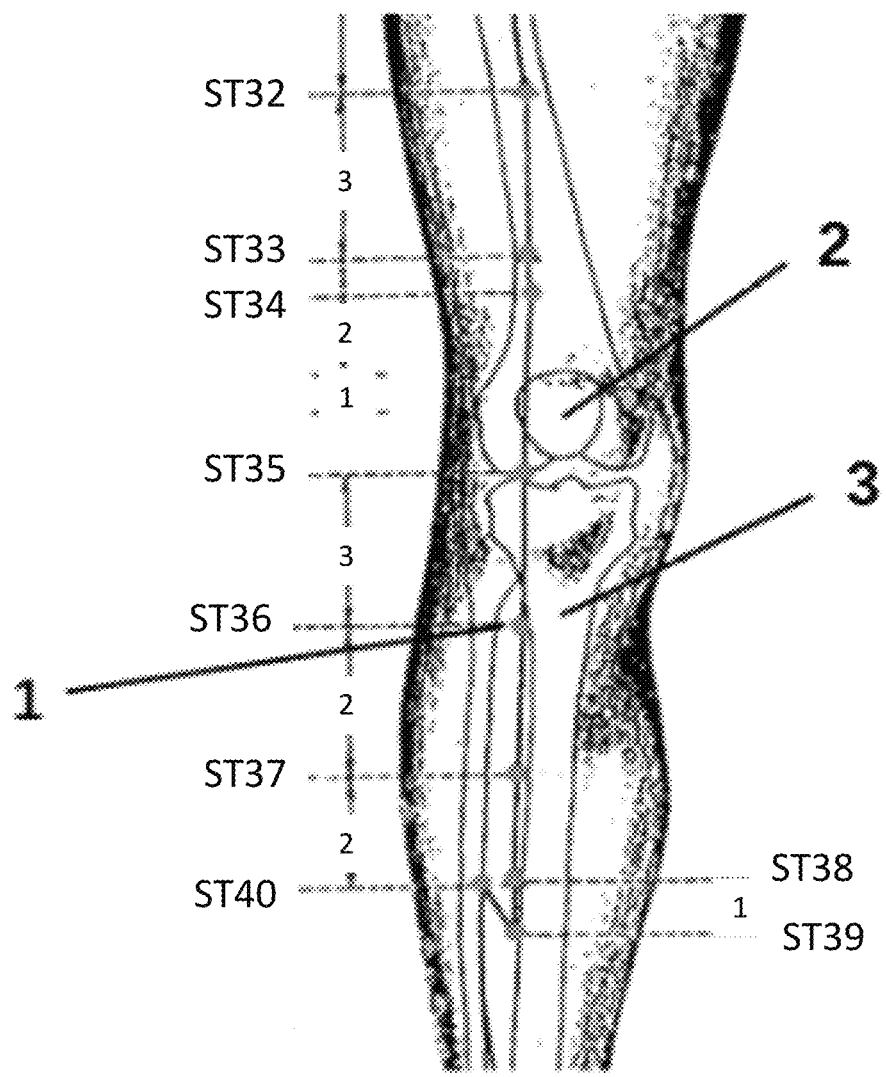
FIG. 2 is a schematic illustration of the location of acupuncture points in the stomach meridian.

FIG. 2 illustrates the location of acupuncture points in the stomach (ST) meridian. The ST36 Zusanli acupoint is located approximately 6 cm distal to the depression below the patella and approximately 2 cm lateral to the anterior ridge of the tibia.

Figure 3:
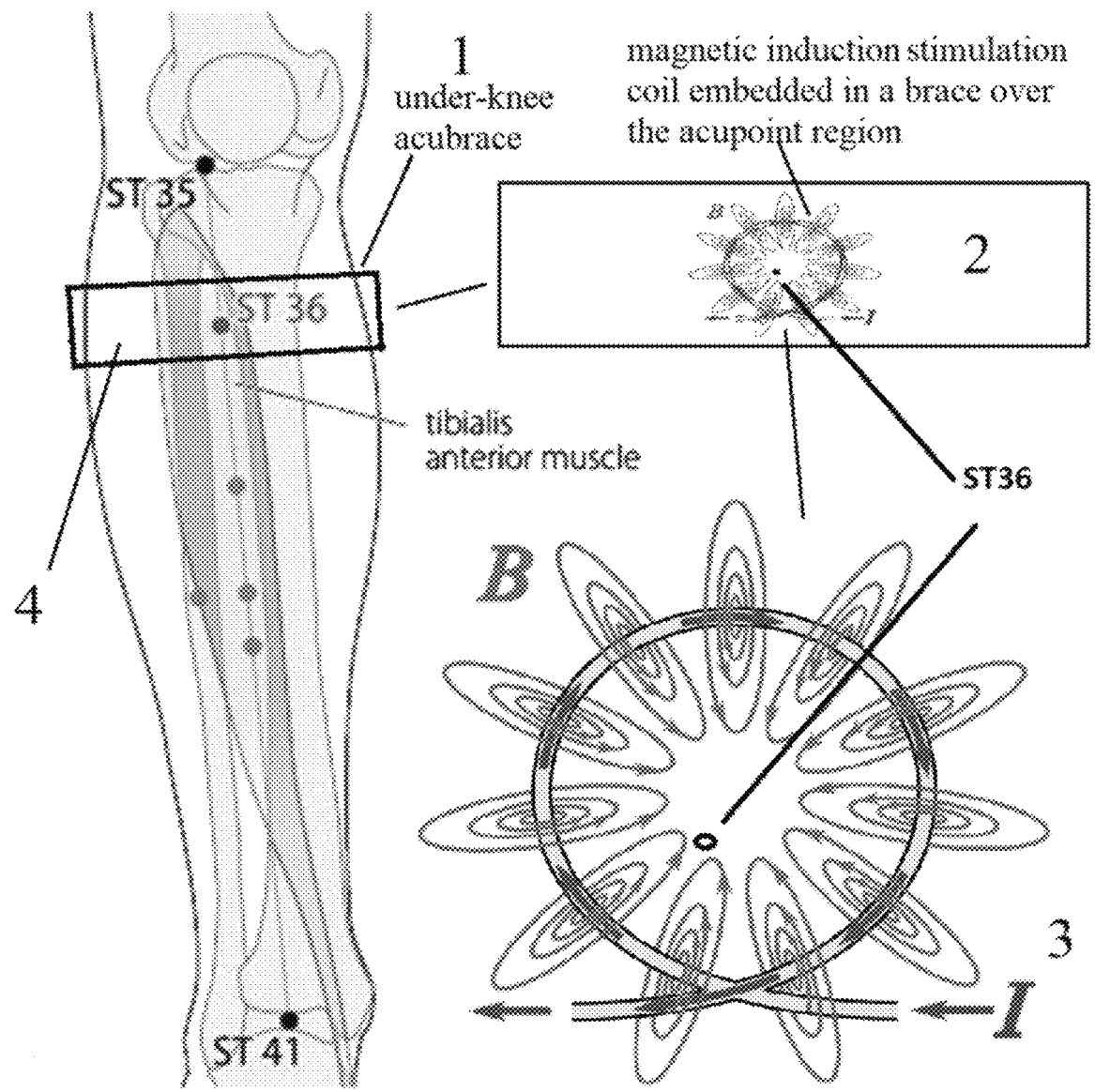
FIG. 3 is a schematic illustration of a magnetic induction coil placed over the acuregion by a brace.
Figure 4:
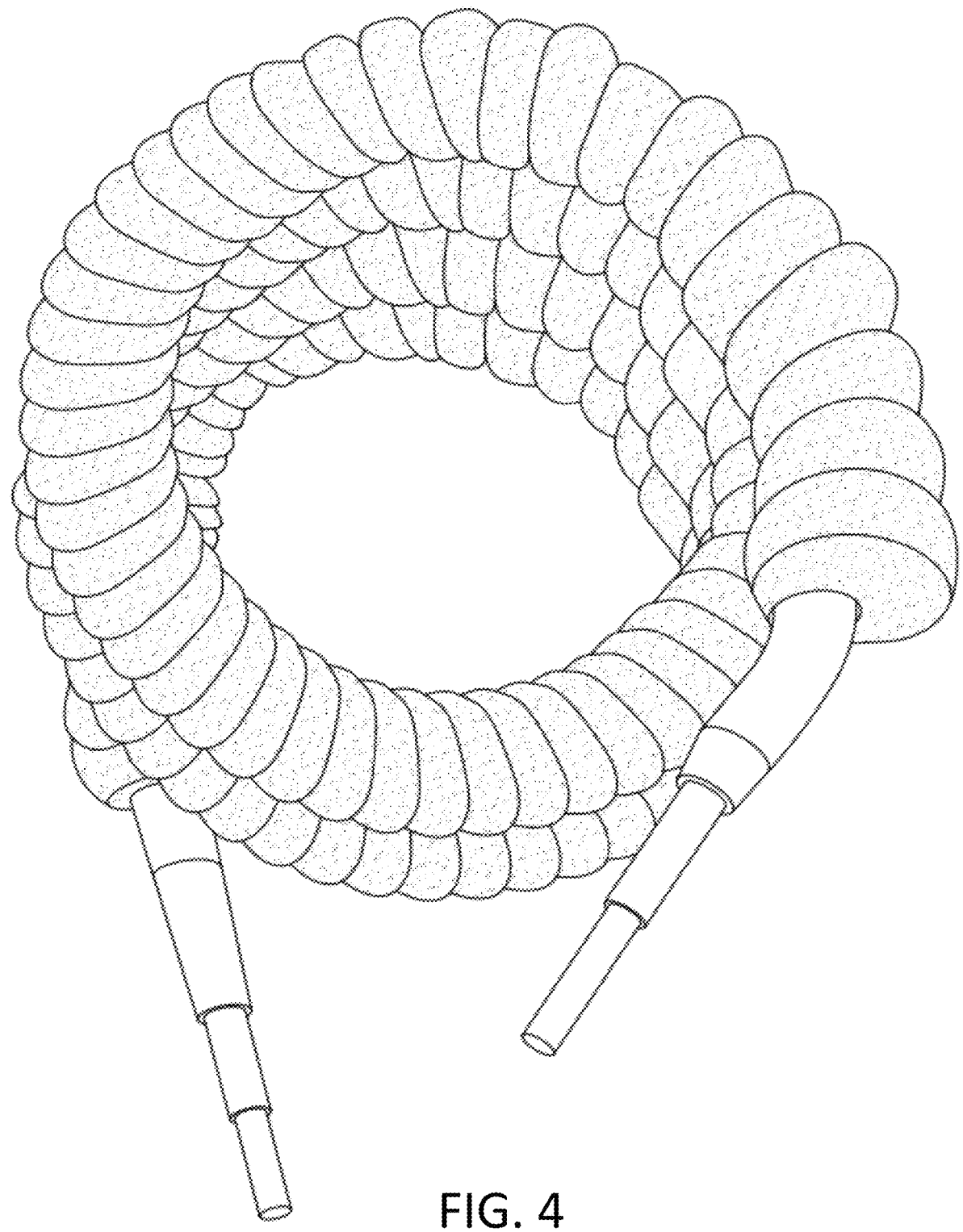
FIG. 4 is a schematic illustration of an embedded magnetic coil in a brace for magnetic stimulation of ST36.

FIG. 3 depicts how, in an example embodiment, a magnetic induction coil is placed over the acuregion by a brace (below-knee in the case of ST36) to allow the magnetic induction to stimulate the acupoint region of interest.

Figure 5:
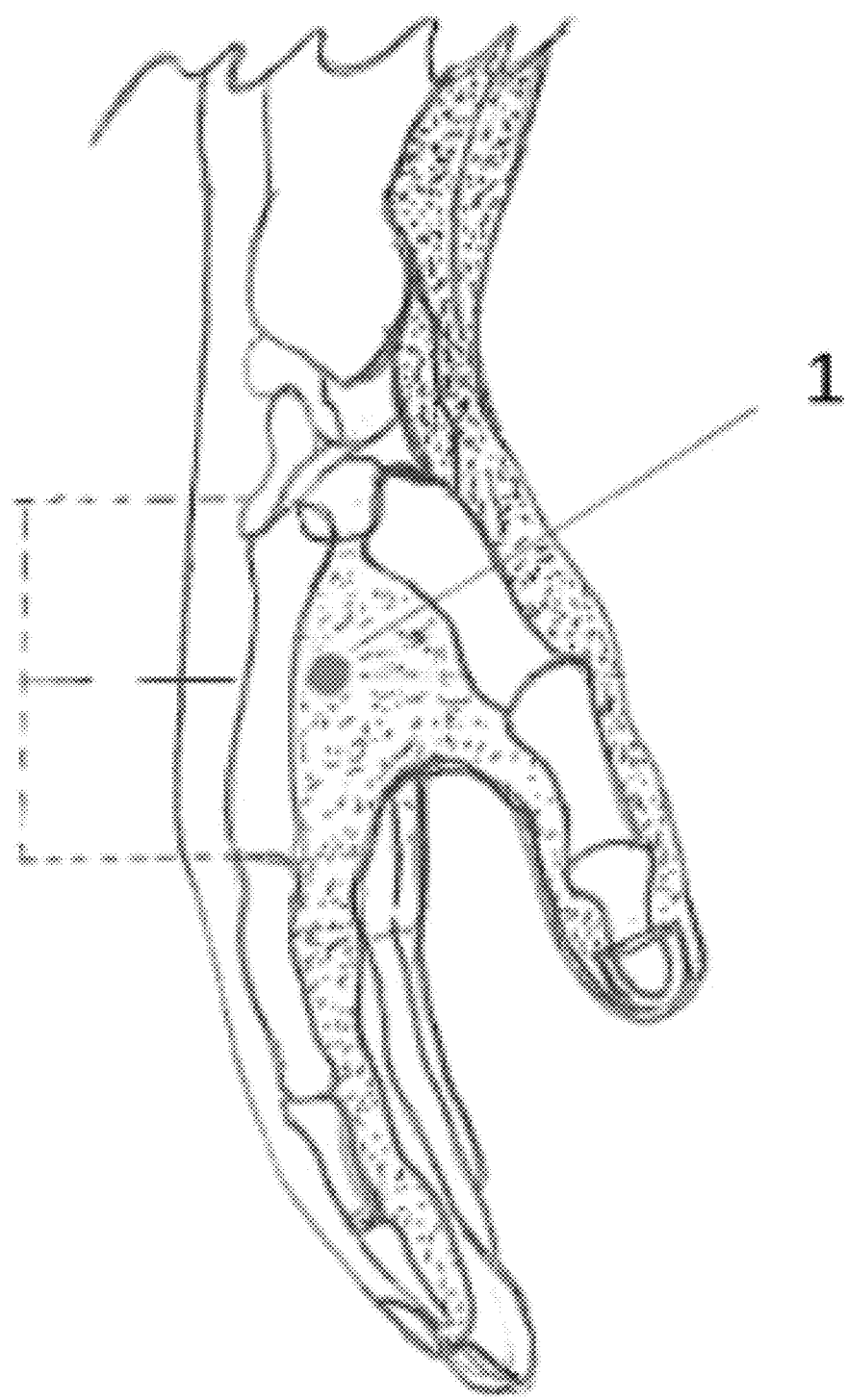
FIG. 5 is a schematic illustration of the location of LI4 Hegu Acupuncture Point.

FIG. 5 shows the LI4 Hegu acupuncture point, part 1, located in the adductor pollicis muscle at the highest point of the web space between the thumb and index finger.

Figure 6:
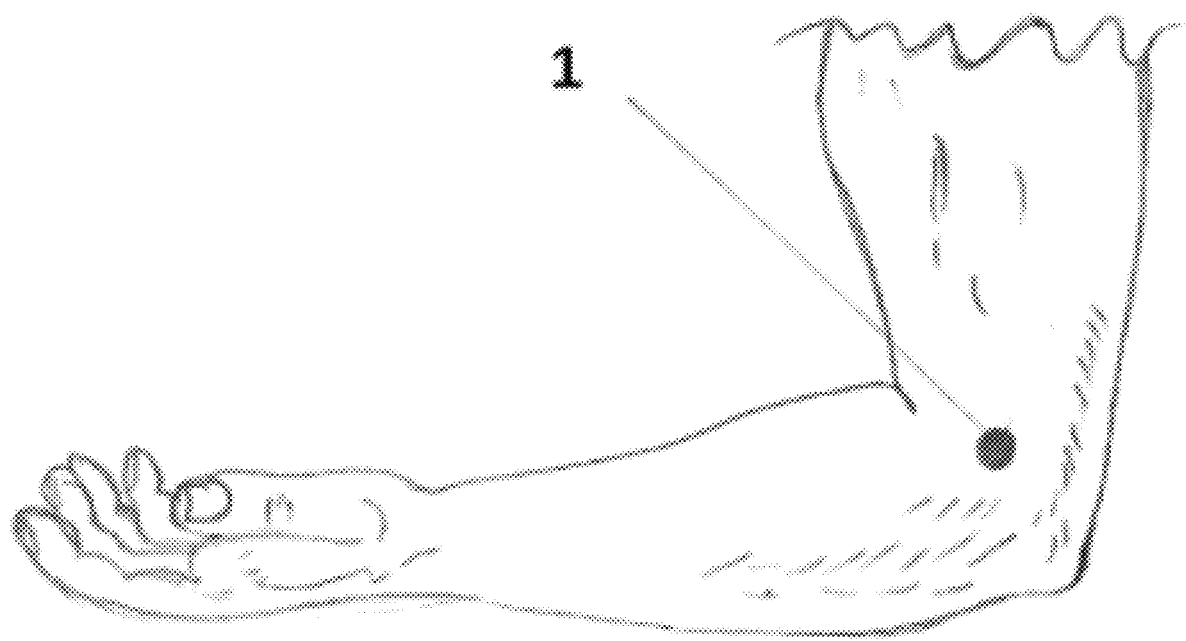
FIG. 6 is a schematic illustration of the location of LI11 Quchi Acupuncture Point.

FIG. 6 shows the LI11 Quchi acupuncture point, part 1, located in the depression at the lateral end of the transverse cubital crease of the elbow, midway between the depression lateral to biceps brachii tendon and the lateral epicondyle of the humerus. This is the motor point of the extensor digitorum communis muscle.

Figure 7:
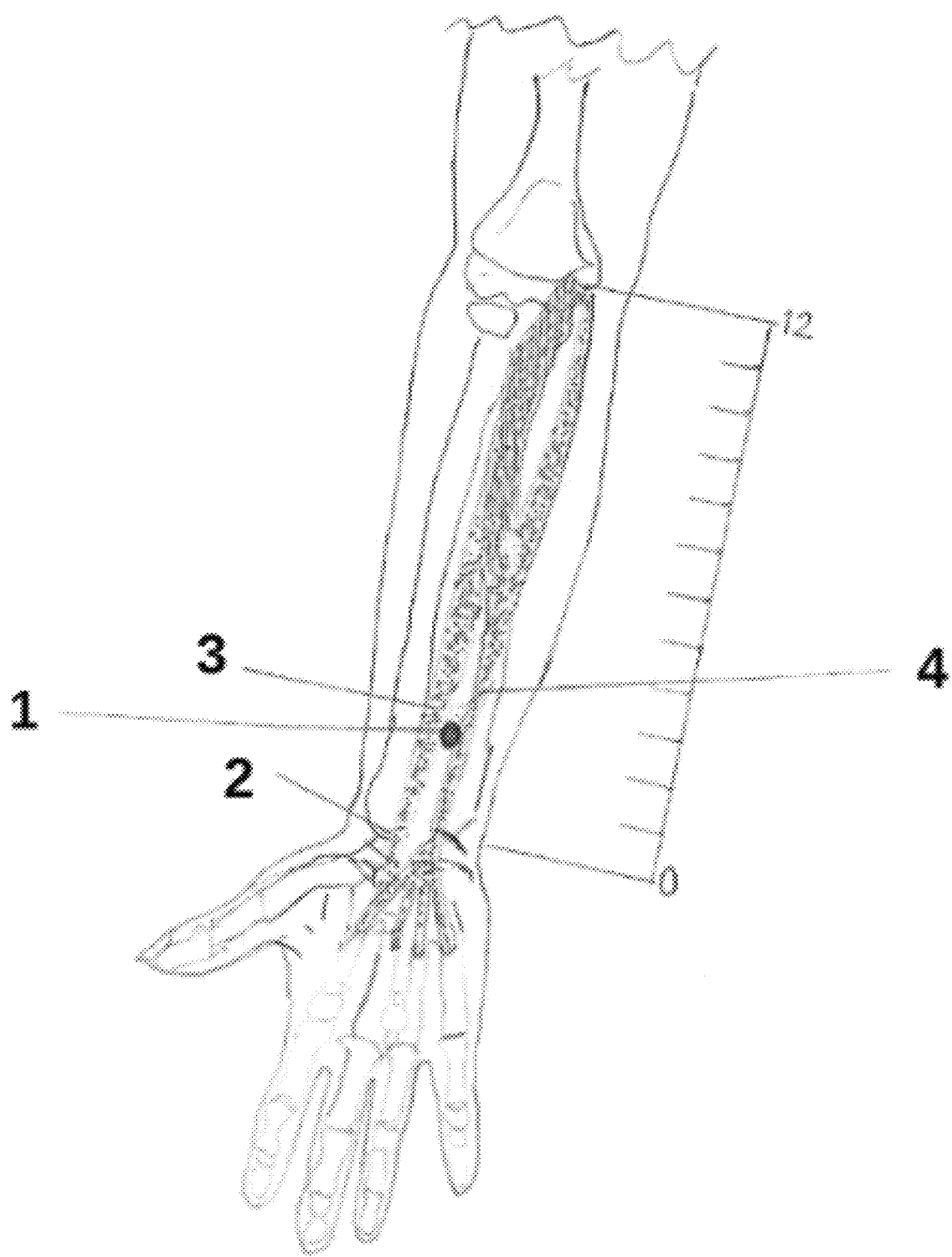
FIG. 7 is a schematic illustration of the location of PC6 Neiguan acupuncture point.

FIG. 7 illustrates the PC6 Neiguan acupuncture point, part 1, located at the center of the anterior forearm, between the tendons of the palmaris longus, part 4, and the flexor carpi radialis muscle, part 3, approximately 6.7 cm proximal to the crease of the wrist, part 2.

Figure 8:
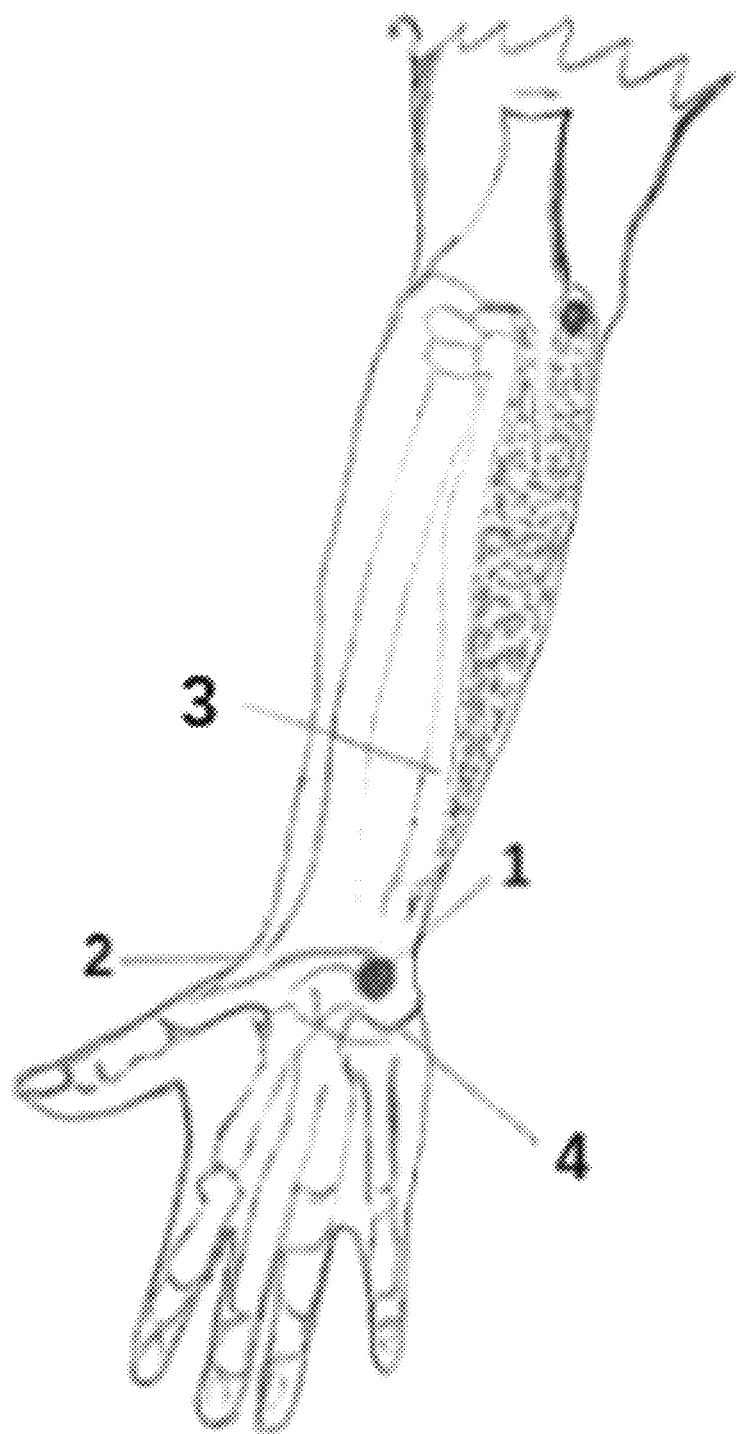
FIG. 8 is a schematic illustration of the location of HT7 Shenmen acupuncture point.

FIG. 8 illustrates the HT7 Shenmen acupuncture point, part 1, located at the medial end of the transverse crease of the wrist, part 2, between the ulna, part 3, and pisiform bone, part 4.

Neurocognitive impairment is responsible for significant morbidity and has had an increasing incidence in the developed world. Dementia from Alzheimer's disease and other causes currently affects 4 million Americans and 44 million people worldwide. GBD 2016 Dementia Collaborators. Global, regional, and national burden of Alzheimer's disease and other dementias, 1990-2016: a systematic analysis for the Global Burden of Disease Study 2016. Lancet Neurol. 2019; 18:88-106. Environmental and lifestyle factors have a large impact. In particular, physical exercise slows the rate of age-related cognitive decline (Bherer L, Erickson K I, Liu-Ambrose T. A review of the effects of physical activity and exercise on cognitive and brain functions in older adults. Journal of Aging Research. 2013:657508), reduces the risk of developing dementia (Blondell S J, Hammersley-Mather R, Lennert Veerman J. Does physical activity prevent cognitive decline and dementia? A systematic review and meta-analysis of longitudinal studies. BMC Public Health. 2014; 14:510), and improves cognition in people who already have dementia (Heyn P, Abreu B C, Ottenbacher K J. The effects of exercise training on elderly persons with cognitive impairment and dementia: a meta-analysis. Arch Phys Med Rehabil. 2004; 85:1694-1704). Physical exercise has considerable benefit for the brain by enhancing the production of brain-derived neurotrophic factor (BDNF) (Wang R, Holsinger R M D. Exercise-induced brain-derived neurotrophic factor expression: Therapeutic implications for Alzheimer's dementia. Ageing Research Reviews. 2018; 48:109-121), preserving and enhancing the brain's blood supply (Trigiani L J, Hamel E. An endothelial link between the benefits of physical exercise and dementia. Journal of Cerebral Blood Flow and Metabolism. 2017; 37:2649-2664), protecting brain cells from apoptosis, increasing the birth of new brain cells (adult neurogenesis) (Kim S-E, Ko I-G, Kim B-K, et al. Treadmill exercise prevents aging-induced failure of memory through an increase in neurogenesis and suppression of apoptosis in rat hippocampus. Experimental Gerontology. 2010; 45:357-365) and, in older adults, increasing the size of the hippocampus (Erickson K I, Voss M W, Shaurya Prakash R, et al. Exercise training increases size of hippocampus and improves memory. PNAS. 2011; 108:3017-3022). However, even minimal physical exercise is unavailable to many people, and especially those most at risk of dementia, due to orthopedic problems, chronic pain, and movement disorders such as Parkinson's disease. Thus, there is a great need for other ways of achieving the same benefit.

Major Depressive Disorder alone affects 6.8% of American adults, entailing an estimated $210 billion in direct medical costs and lost workplace productivity, and accounts for approximately 50% of suicides. Greenberg P E, Fournier A-A, Sisitsky T, Pike C T, Kessler R C. The economic burden of adults with Major Depressive Disorder in the United States (2005 and 2010). J Clin Psychiatry. 2015; 76:155-162. Even excluding suicide, Major Depressive Disorder is associated with a ten-year reduction in life expectancy. Laursen T M, Musliner K L, Benros M E, Vestergaard M, Munk-Olsen T. Mortality and life expectancy in persons with severe unipolar depression. J Affect Disord. 2016; 193:203-207. Worldwide, the prevalence of depression appears to have increased over the past thirty years. Global Burden of Disease Study 2013 Collaborators. Global, regional, and national incidence, prevalence, and years lived with disability for 301 acute and chronic diseases and injuries in 188 countries, 1990-2013: A systematic analysis for the Global Burden of Disease Study 2013. Lancet. 2015; 386:743-800.

Of note, physical exercise is an empirically supported treatment for Major Depressive Disorder; controlled clinical studies show moderate or large effect sizes, with little indication of publication bias. Morres I D, Hatzigeorgiadis A, Stathi A, Comoutos N, Arpin-Cribbie C, Krommidas C, Theodorakis Y. Aerobic exercise for adult patients with major depressive disorder in mental health services: a systematic review and meta-analysis. Depress Anxiety. 2019; 36:39-53. This is likely because of the favorable effects of physical exercise on the brain, noted above, and because exercise strengthens several homeostatic systems that are dysregulated in depression, including the hypothalamic-pituitary-adrenal axis, the sympathetic-parasympathetic autonomic balance, and regulation of the inflammatory response. Belvederi Murri M, Ekkekakis P, Magagnoli M, Zampogna D, Cattedra S, Capobianco L, et al. Physical exercise in major depression: reducing the mortality gap while improving clinical outcomes. Frontiers in Psychiatry. 2019; 9:762.

Here, too, however, exercise is often unavailable. The psychomotor slowing, fatigue, sleep disruption, and loss of motivation inherent in depression, as well as comorbidities such as chronic pain, make exercise difficult to achieve for depressed individuals. Thus, exercise programs show a high dropout rate among patients with Major Depressive Disorder. Tobi P, Kemp P, Schmidt E. Cohort differences in exercise adherence among primary care patients referred for mental health versus physical health conditions. Primary Health Care Research and Development. 2017; 18:463-471. Again, there is a great need for other ways of achieving the same benefit.

Post-Covid Cognitive Impairment. As of Sep. 25, 2022, there had been 612 million confirmed cases of Covid-19 worldwide (World Health Organization. https://www.who.int/publications/m/item/weekly-epidemiological-update-on-covid-19-28-september-2022), with the actual positive case number estimated to be tenfold higher. Ceban F, Ling S, Lui L M W, Lee Y, Gill H, Teopiz K M, et al. Fatigue and cognitive impairment in Post-COVID-19 Syndrome: A systematic review and meta-analysis. Brain Behav Immun. 2022; 101:93-135. Large-scale meta-analyses indicate that 22% of Covid-19 patents experience cognitive impairment three months after diagnosis. Importantly, this number remains at 21% six or more months after diagnosis, implying that there is little or no spontaneous remission. The cognitive symptoms primarily affect memory, attention, and executive functioning.

Prospective volumetric MRI data shows global brain atrophy following Covid-19. Douaud G, Lee S, Alfaro-Almagro F, Arthofer C, Wang C, McCarthy P, et al. SARS-COV-2 is associated with changes in brain structure in UK Biobank. Nature. 2022; 604:697-707. A degree of overlap with Alzheimer's disease is suggested in that the hippocampus, involved in memory formation, is one of the main areas affected by volume loss. Najt P, Richards H L, Fortune D G. Brain imaging in patients with COVID-19: a systematic review. Brain Behav Immun Health. 2021; 16:100290. Moreover, patients with preexisting Alzheimer's disease show more rapid deterioration after contracting Covid-19. Frontera J A, Sabadia S, Laichan R, Fang T, Flusty B, Millar-Vernetti P, et al. A prospective study of neurologic disorders in hospitalized patients with COVID-19 in New York City. Neurology. 2021; 96: e575-e586.

Underlying the similarity, animal and post-mortem studies suggest that Covid-19, like Alzheimer's disease, involves a reduction in adult neurogenesis (Bayat A-H, Azimi H, Moghaddam M H, Ebrahimi V, Fathi M, Vakili K, et al. COVID-19 causes neuronal degeneration and reduces neurogenesis in human hippocampus. Apoptosis. 2022. Doi: 10.1007/s10495-022-01754-9.)(Kumaria A, Noah A, Kirkman M A. Does covid-19 impair endogenous neurogenesis? J Clin Neurosci. 2022; 105:79-85.) which may be a result of direct viral effects on neural stem cells or through cytokine/chemokine-initiated neuroinflammation. Fernández-Castañeda A, Lu P, Geraghty A C, Song E, Lee M-H, Wood J, et al. Mild respiratory COVID can cause multi-lineage neural cell and myelin dysregulation. Cell. 2022; 185:2452-2468.

Thus, there is a strong need for safe, noninvasive means of boosting adult neurogenesis to treat post-Covid cognitive impairment. However, because 32% of Covid patients also have prominent fatigue three months or more after diagnosis, and because this fatigue often involves post-exertional malaise, exercise may not be a feasible treatment. The present invention, by replicating the effects of exercise without increasing fatigue, can likely fill this need.

Post-Intensive Care Unit Syndrome. In the United States, millions of patients are admitted to intensive care units each year with critical illness. Critical illness is associated with the development of a syndrome known as post-intensive care unit syndrome (aka PICS). PICS manifests as acquired weakness, cognitive or brain dysfunction (delirium), and mental health problems. The incidence of ICU-acquired weakness is 33% in ventilated patients, 50% in patients admitted with sepsis, and up to 50% in inpatients who stay in the ICU for at least 1 week. Cognitive or brain dysfunction can affect up to 80% of patients who require ICU admission. Patients with sepsis associated PICS can also be affected by PTSD and depression with an estimated prevalence of 16% and 28% respectively. PICS can have a significant impact on an individual's functional status, and as a result, a significant proportion of patients suffering from PICS are unable to return to their baseline level of function after their ICU admission. One expert referred to the post sepsis ICU syndrome specifically as, "a hidden public health disaster." Ehlenbach W J, Gilmore-Bykovskyi A, Repplinger M D, Westergaard R P, Jacobs E A, Kind A J H, Smith, M. Sepsis Survivors Admitted to Skilled Nursing Facilities: Cognitive Impairment, Activities of Daily Living Dependence, and Survival. Critical Care Medicine. 2019; 46(1):37-44. Angus, D. The lingering consequences of sepsis: a hidden public health disaster? JAMA.2010; 304(16): 1833-4. https://www.sccm.org/MyICUCare/THRIVE/Post-intensive-Care-Syndrome. Accessed on Oct. 26, 2022.

The administration of steady heat and magnetic field stimulation to ST-36 can be utilized both as a primary prevention as well as treatment strategy for post-ICU syndrome associated cognitive dysfunction, delirium, and depression. The impact of such a modality of treatment, which could be performed easily and non-invasively in the hospital and/or ICU setting, would be significant in terms of reducing the overall burden associated with PICS.

Post-Chemotherapy-Induced Cognitive Impairment. In approximately one-third to two-thirds of patients receiving chemotherapy for cancer, the treatment causes cognitive impairment (Kotb M G, Soliman A E R, Ibrahim R I, Said R M M, El Din M M W. Chemotherapy-induced cognitive impairment in hematological malignancies. Egyptian Journal of Neurology, Psychiatry, and Neurosurgery. 2019; 55:56.) (Whittaker A L, George R P, O'Malley L. Prevalence of cognitive impairment following chemotherapy treatment for breast cancer: a systematic review and meta-analysis. Sci Rep. 2022; 12:2135), with effects persisting for greater than ten years. Stouten-Kemperman M M, de Ruiter M B, Boogerd W, Veltman D J, Reneman L, Schagen S B. Very late treatment-related alterations in brain function of breast cancer survivors. J Int Neuropsych Soc. 2015; 21:50-61. Short-term and long-term memory, executive functioning, and processing speed are particularly affected. Matsos A, Johnston I N. Chemotherapy-induced cognitive impairments: A systematic review of the animal literature. Neurosci Biobehav Rev. 2019; 102:382-399. Nearly all chemotherapy agents have been implicated, including 5-fluorouracil, cisplatin, doxorubicin, methotrexate, and vincristine.

Although a number of mechanisms have been hypothesized, a strong overlap of the pathophysiology of chemotherapy-induced cognitive impairment with Alzheimer's disease is suggested: (1) Symptomatically, short-term memory is the cognitive domain most consistently affected; (2) Anatomically, the dentate gyrus of the hippocampus, involved in memory formation, is physically smaller even 18 years after chemotherapy (Apple A C, Ryals A J, Alpert K I, Wagner L I, Shih P A, Dokucu M, Cella D, Penedo F J, Voss J L, Wang L. Subtle hippocampal deformities in breast cancer survivors with reduced episodic memory and self-reported cognitive concerns. Neuroimage Clin. 2017; 14:685-691.) (3) Physiologically, neural stem and progenitor cells show decreased proliferation and survival (decreased adult neurogenesis; and (4) pharmacologically, there is symptomatic improvement in chemotherapy-induced cognitive impairment with the Alzheimer's medication donepezil. Lim I, Joung H Y, Yu A R, Shim I, Kim J S. PET evidence of the effect of donepezil on cognitive performance in an animal model of chemobrain. Biomed Res Int. 2016; 2016: 6945415. Winocur G, Binns M A, Tannock I. Donepezil reduces cognitive impairment associated with anti-cancer drugs in a mouse model. Neuropharmacology. 2011; 61:1222-1228.

Importantly, as in Alzheimer's disease, physical exercise helps reverse chemotherapy-induced cognitive impairment (Winocur G, Wojtowicz J M, Huang J, Tannock I F. Physical exercise prevents suppression of hippocampal neurogenesis and reduces cognitive impairment in chemotherapy-treated rats. Psychopharmacology. 2014; 231:2311-2320.) through a mechanism of action that includes increased neurogenesis. It is therefore highly likely that an exercise mimetic that increases neurogenesis, such as stimulation of acupoints, will help reverse chemotherapy-induced cognitive impairment.

For the beneficial adaptations of the brain and body to physical exercise to occur, the exercise must set in motion a sequence of signaling events. It is likely that some of these events are initiated by pressure-sensitive detectors that occur naturally in the muscles, overlying fascia, and nearby nerves and connective tissue. These physiological "exercise detectors" coincide with a number of acupuncture points.

In particular, the Zusanli or ST36 acupoint is located at the anterolateral lower leg, approximately 6 cm distal to the depression below the patella and approximately 2 cm lateral to the anterior ridge of the tibia (see FIG. 3). Li P, Tjen-A-Looi S C, Cheng L, Liu D, Painovich J, Vinjamury S, Longhurst J C. Long-lasting reduction of blood pressure by electroacupuncture in patients with hypertension: randomized controlled trial. Med Acupunct. 2015; 27:253-265. This acupoint includes subcutaneous connective tissue, a portion of the proximal anterior tibialis muscle, the overlying fascia, and a nerve trunk of the deep peroneal nerve. Wu, W-Y., Chen, W-H, Hsieh C-L, Lin Y-W. Abundant expression and functional participation of TRPV1 at Zusanli acupoint (ST36) in mice: mechanosensitive TRPV1 as an "acupuncture responding channel." BMC Complement Altern Med. 2014; 14:96.

This point contains an unusually high density, relative to a control, non-acupuncture point, of TRPV1, TRPV4, and ASIC3 cation channels, which transduce physical stimuli into biological signals. Among these, stimulation of the TRPV1 channels appears to be responsible for the effects of acupuncture. TRPV1 ion channels can be activated by mechanical or chemical stimulation, or by electricity, but first and foremost they are activated by heating to temperatures above 43° C. Caterina, M. J. et al. The capsaicin receptor: a heat-activated ion channel in the pain pathway. Nature. 1997; 389:816-824.

Electroacupuncture stimulation, delivered through acupuncture needles inserted into this point, is generally just below motor threshold: 1 mA at 2 Hz for 20 minutes once a day. Stimulation of the correct point gives a de Qi ("obtaining qi") sensation of paresthesias, heaviness, distension, or mild soreness.

Similar to exercise, stimulation of this acupuncture point appears to elicit a range of neuroprotective and neurorestorative processes. Thus, there is evidence that activation of the ST36 acupoint increases serotonin content of the dorsal raphe nucleus (Wu Y-Y, Jiang Y-L, He X-F, Zhao X-Y, Shao X-M, Sun J, Shen Z, Shou S-Y, Wei J-J, Ye J-Y, Yan S-S, Fang J-Q. 5-HT in the dorsal raphe nucleus is involved in the effects of 100-Hz electro-acupuncture on the pain-depression dyad in rats. Exp Ther Med. 2017; 14:107-114), raises serum levels of brain-derived neurotrophic factor (BDNF) (Tao J, Chen B, Gao Y, Yang S, Huang J, Jiang X, Wu Y, Peng J, Hong Z, Chen L. Electroacupuncture enhances hippocampal NSCs proliferation in cerebral ischemia-reperfusion injured rats via activation of notch signaling pathway. Int J Neurosci. 2014; 124:204-212), stimulates hippocampal neurogenesis after ischemia, suppresses apoptosis of neurons (Chavez L M, Huang S-S, MacDonald I, Lin J-G, Lee Y-C, Chen Y-H. Mechanisms of acupuncture therapy in ischemic stroke rehabilitation: a literature review of basic studies. Int J Mol Sci. 2017; 18:2270), and may raise levels of activated endothelial nitric oxide synthase, (eNOS), calcitonin gene-related peptide (CGRP) (Lee C H, Kim D-K, Yook T-H, Sasaki M, Kitamura N. Effectiveness of electroacupuncture at Zusanli (ST36) on the immunohistochemical density of enteroendocrine cells related to gastrointestinal function. J Acupunct Meridian Stud. 2012; 5:63-71.) and brain antioxidant defenses.

Thus, stimulation of ST36 is part of traditional acupuncture protocols for stroke, Alzheimer's disease (Yu C-C, MA C-Y, Wang H, King L-H, Zhao Y, Shen F, Wu M. Effects of acupuncture on Alzheimer's disease: evidence from neuroimaging studies. Chin J Integr Med. 2018. DOI: 10.1007/s11655-018-2993-3), and Parkinson's disease. In clinical studies it has been part of protocols showing effectiveness for reducing cognitive impairment from chemotherapy in breast cancer patients and postoperative cognitive dysfunction in the elderly. Nam M-H, Ahn K S, Choi S-H. Acupuncture stimulation induces neurogenesis in adult brain. Int Rev Neurobiol. 2013; 111:67-90. Tong T, Pei C, Chen J, Lv Q, Zhang F, Cheng Z. Efficacy of acupuncture therapy for chemotherapy-related cognitive impairment in breast cancer patients. Med Sci Monit. 2018; 24:2919-2927.

In addition, stimulation of ST36 may facilitate brain recovery by protecting the blood vessel endothelium. Thus, activation of ST36 appears to treat hypertension by reducing oxidative and nitrosative stress in serum and blood vessel endothelium, reducing serum levels of angiotensin and the activity of oxidant-producing NADPH oxidase, and increasing the production and availability of nitric oxide. Leung S B, Zhang H, Lau C W, Lin Z-X. Attenuation of blood pressure in spontaneously hypertensive rats by acupuncture was associated with reduction in oxidative stress and improvement from endothelial dysfunction. Chin Med. 2016; 11:38. Moreover, electrical stimulation of ST36 on one leg strengthens the anterior tibialis muscle on both legs, implying an effect mediated by the central nervous system. Huang L-P, Zhou S, Lu Z, Tian Q, Li X, Cao L-J, Yu J-h, Wang H. Bilateral effect of unilateral electroacupuncture on muscle strength. J Altern Complement Med. 2007; 13:539-546.

Similarly, stimulation of this acupuncture point appears to elicit other processes thought to be beneficial for depression. Thus, in an animal model of depression, acupuncture at ST36 and CV4 reduced hypothalamic-pituitary-adrenal axis over-activity and raised the concentration of serotonin and the serotonin 1a receptor in the hippocampus, changes that were correlated with an improvement in depression. Le J-J, Yi T, Qi L, Li J, Shao L, Dong J-C. Electroacupuncture regulate hypothalamic-pituitary-adrenal axis and enhance hippocampal serotonin system in a rat model of depression. Neuroscience Letters. 2016; 615:66-71. In people, acupuncture at ST36 and DU20 raises serum levels of glial cell line-derived neurotrophic factor (GDNF) in concert with an improvement in depression. Sun H, Zhao H, Ma C, Bao F, Zhang J, Wang D-H, et al. Effects of electroacupuncture on depression and the production of glial cell line-derived neurotrophic factor compared with fluoxetine: a randomized controlled pilot study. Journal of Alternative and Complementary Medicine. 2013; 19:733-739.

Depression, in fact, is the second most common indication for acupuncture treatment in the US, slightly below low back pain. Wang H, Yang G, Wang S, Zheng X, Zhang W, Li Y. The most commonly treated acupuncture indications in the United States: a cross-sectional study. American Journal of Chinese Medicine. 2018; 46:1387-1419. Acupuncture has received empirical support for the treatment of depression, although the clinical trial literature is still at an early stage in terms of methodological quality. Smith C A, Armour M, Lee M S, Wang L Q, Hay P J. Acupuncture for depression. Cochrane Database Syst Rev. 2018; 3:CD004046. In a randomized clinical trial it was as effective as 20 mg fluoxetine. Like exercise, acupuncture appears to have more rapid onset of action than fluoxetine. Thus, stimulation of ST36 is part of clinical studies showing effectiveness of acupuncture for depression, including post-stroke depression. Youn J-I, Sung K-K, Song B-K, Kim M, Lee S. Effects of electro-acupuncture therapy on post-stroke depression in patients with different degrees of motor function impairments: a pilot study. J Phys Ther Sci. 2013; 25:725-728. Li X B, Wang J, Xu A D, Huang J M, Meng L Q, Huang R Y, Xu J. Clinical effects and safety of electroacupuncture for the treatment of post-stroke depression: a systematic review and meta-analysis of randomised controlled trials. Acupunct Med. 2018; 36:284-293.

Moreover, depression is a risk factor for cardiovascular disease, which likely accounts for some of the excess mortality in individuals with Major Depressive Disorder. Belvederi Murri M, Ekkekakis P, Magagnoli M, Zampogna D, Cattedra S, Capobianco L, et al. Physical exercise in major depression: reducing the mortality gap while improving clinical outcomes. Frontiers in Psychiatry. 2019; 9:762. Thus, the beneficial effects on the endothelium from stimulating ST36, noted above, may be relevant to protecting depressed individuals from cardiovascular comorbidity.

Note that these physiological functions of ST36 closely resemble those of aerobic exercise such as walking. For example, the neurogenesis due to acupuncture at ST36, like that due to exercise, is specifically in the dentate gyrus of the hippocampus, where the new neurons allow the formation of new spatial maps—crucial to survival when one is walking in the jungle or forest.

This does not seem surprising, as the anterior tibialis muscle, where ST36 is located, participates in walking, tilting the foot upward (ankle dorsiflexion) while the leg is swinging forward so that the foot lands at the heel, thus reducing forces on the knee joint. Simonsen E B. Contributions to the understanding of gait control. Dan Med J. 2011; 61 (4): B4823. Through eccentric contraction, the anterior tibialis also stabilizes the ankle, facilitating contact of the foot with the ground. Ruiz-Muñoz M, Cuesta-Vargas A I. Electromyography and sonomyography analysis of the tibialis anterior: a cross sectional study. J Foot Ankle Res. 2014; 7:11. On electromyography with surface electrodes, maximum firing of this muscle is during the contact phase, shortly after heel strike (i.e., at approximately 14% into the gait cycle). Scott L A, Murley G S, Wickham J B. The influence of footwear on the electromyographic activity of selected lower limb muscles during walking. J Electromyogr Kinesiol. 2012; 22:1010-1016. This is also a time when forces at the knee joint (the tibiofemoral capsule) are high. Shelburne K B, Torry M R, Pandy M G. Muscle, ligament, and joint-contact forces at the knee during walking. Med Sci Sports Exerc. 2005; 37:1948-1956. Thus, the pressure sensors at ST36, in the upper anterior tibialis, would seem well positioned to detect the forces associated with walking and communicate them to the brain.

Thus, the hypothesis is presented that many beneficial aspects of exercise (walking) are mediated through the central nervous system and can be replicated by communicating to the brain that one is walking. Moreover, this signal to the brain can be achieved by external stimulation of the ST36 acupuncture point. The combination of heat and an oscillatory magnetic field is used specifically because (1) the ST36 acupoint consists of TRPV1 ion channels that open when heated to above 43° C.; (2) an oscillatory magnetic field activates the open channels by inducing ion currents through them; (3) oscillation maximizes stimulation by preventing receptor fatigue; and (4) natural stimulation of the acupoint through exercise is oscillatory—for example, walking at normal speed involves tensing the anterior tibialis at approximately 2 Hz.

Of course, in the natural world, physical exercise and the attendant somatic stimulation rarely involves a single muscle in isolation. A number of other acupoints have been shown to enhance growth factor production, encourage adult neurogenesis, protect brain cells from apoptosis, and facilitate recovery from insults to the brain, as well as raise serotonin levels in the cortex and ameliorate depression.

These points include Hegu (LI4), Quchi (LI11), Neiguan (PC6), and Shenmen (HT7). Hegu is located in the adductor pollicis muscle, which governs the opposable thumb, bringing it into contact with the plane of the hand. Quchi is at the motor point of the extensor digitorum communis muscle, which extends the fingers and fires strongly to stabilize the wrist when gripping. Neiguan is towards the distal end of the flexor digitorum superficialis muscle, which flexes the fingers and wrist. Shenmen is in the distal anterior forearm, at the ulnar side of the wrist crease. It is located in the tendon of the flexor carpi ulnaris muscle (Chapple W. Proposed catalog of the neuroanatomy and the stratified anatomy for the 361 acupuncture points of 14 channels. J Acupunct Meridian Stud. 2013; 6:270-274. Deadman P, Al-Khafaji M, Kevin Baker K. Manual of acupuncture. Hove, East Sussex, England: Journal of Chinese Medicine Publications; 2007).

All four muscles are active during use of the hands, and grasping in particular. Consistent with this, grip strength has been found in the scientific literature to correlate with cognitive performance across a range of domains in the present, and to predict future cognitive decline. Firth J, Firth J A, Stubbs B, Vancampfort D, Schuch FitBit, Hallgren M, et al. Association between muscular strength and cognition in people with major depression and bipolar disorder and healthy controls. JAMA Psychiatry. 2018; 75:740-746. Veronese N, Stubbs B, Trevisan C, Bolzetta F, Rui M D, Solmi M, et al. What physical performance measures predict incident cognitive decline among intact older adults? A 4.4-year follow-up study. Exp Gerontol. 2016; 80:110-118. Similarly, grip strength seems to correlate inversely with current depression and to predict future new-onset depression. Fukumori N, Yamamoto Y, Takegami M, Yamazaki S, Onishi Y, Sekiguchi M, Fukuhara S. Association between hand-grip strength and depressive symptoms: Locomotive Syndrome and Health Outcomes in Aizu Cohort Study (LOHAS). Age Ageing. 2015; 44:592-598.

FIGS. 5, 6, 7, and 8 show the location of Hegu, Quchi, Neiguan, and Shenmen, respectively.

These acupoints can be presumed to be circular, 2-4 mm in diameter. They can also be presumed to consist of TRPV1 ion channels. Abraham T S, Chen M-L, Ma S-X. TRPV1 expression in acupuncture points: response to electroacupuncture stimulation. J Chem Neuroanat. 2011; 41:129-136. Kawakita K, Shinbara H, Imai K, Fukuda F, Yano T, Kuriyama K. How do acupuncture and moxibustion act? Focusing on the progress in Japanese acupuncture research. J Pharmacol Sci. 2006; 100:443-459. The present invention includes combined noninvasive heating and pulsed magnetic activation of one or more of these points, in addition to or instead of ST36.

Temperature Parameters. The above noted acupuncture points are most likely made up of TRPV1 ion channels, which can be activated by mechanical stimulation (e.g., in acupuncture) or electricity (e.g., in electroacupuncture) but which are primarily detectors of noxious levels of heat.

The stimulus-response curve of TRPV1 has been well mapped out. It begins generating excitatory currents at 44-52° C. This increases sharply at around 48° C. and reaches maximum at 52° C. Caterina M J, Rosen T A, Tominaga M, Brake A J, Julius D. A capsaicin-receptor homologue with a high threshold for noxious heat. Nature. 1999; 398:436-441.

Tissue damage is not a risk with the parameters used in this device. Skin would need to be exposed to 45° C. for 200 minutes continuously before sustaining tissue damage, and for muscle, tissue damage would not begin until 400 minutes of exposure. Dewhirst M W, Viglianti B L, Lora-Michiels M, Hanson M, Hoopes P J. Basic principles of thermal dosimetry and thermal thresholds for tissue damage from hyperthermia. Int J Hyperthermia. 2003; 19:267-294. At 50° C. the corresponding parameters are 4 minutes for skin and 5 minutes for muscle. By keeping stimulation close to 44-52° C. and per-session stimulation time to 30 minutes or less, necrosis would not obtain.

However, TRPV1 transduces noxious levels of heat, and by definition underlies heat pain. Contact heat pain begins after 6 seconds of continuous exposure at 45° C. and 2 seconds of exposure at 50° C. However, for thermal radiation, the pain threshold is approximately 45° C., and for individuals with lower thresholds the evoked pain at 44-52° C. is minimal. Hardy J D, Goodell H, Wolff H G. The influence of skin temperature upon the pain threshold as evoked by thermal radiation. Science. 1951; 114:149-150. Thus, a temperature of 44-52° C. would avoid causing significant pain. At 44-52° C., TRPV1 is 24% open, as a percentage of peak current density (Caterina M J, Rosen T A, Tominaga M, Brake A J, Julius D. A capsaicin-receptor homologue with a high threshold for noxious heat. Nature. 1999; 398:436-441), allowing for ion flow to be induced through it by magnetic stimulation. Note that acupuncture itself needs to be mildly painful to be effective—the "de Qi" sensation is a mild, heavy, dull soreness at the site of needle insertion.

Magnetic Stimulation Parameters. Appropriate parameters for magnetic stimulation of acupoints can be deduced from studies of the effects of transcranial magnetic stimulation of motor cortex in the brain on motor evoked potentials. Motor cortex is the at same depth relative to the skin surface as ST36. Deng Z-D, Lisanby S H, Peterchev A V. Coil design considerations for deep transcranial magnetic stimulation. Clinical Neurophysiology. 2014; 125:1202-1212. Motor cortex is activated by glutamatergic control of ion channels that, like TRPV1, are calcium channels specifically. Klomjai W, Katz R, Lackmy-Vallée A. Basic principles of transcranial magnetic stimulation (TMS) and repetitive TMS (rTMS). Annals of Physical and Rehabilitation Medicine. 2015; 58:208-213. Optimal activation of motor cortex is achieved with short bursts of 1 to 5 Hz magnetic stimulation with a field strength of up to 1.5 Tesla. Di Lazzaro V, Dileone M, Pilato F, Capone F, Musumeci G, Ranieri F, Ricci V, Bria P, Di lorio R, de Waure C, Pasqualetti P, Profice P. Modulation of motor cortex neuronal networks by rTMS: comparison of local and remote effects of six different protocols of stimulation. Journal of Neurophysiology. 2011; 105:2150-2156. These same parameters should be correct for activation of ST36 as well. These parameters optimize the magnetic stimulation for movement of ions through the acupoint and do not lead to significant magnetic induction heating of the acupoint.

Anatomical Parameters. In traditional Chinese medicine, acupuncture needles are inserted at ST36 to a depth of between 0.92 and 4.60 cm. Superficial insertion (2-3 mm) is used as a control condition in acupuncture studies and has no effect. Insertion beyond 2.58 cm can entail damage to blood vessels and nerves so a depth of 1.25 cm should be safe while being in the effective range. The same depth is appropriate for LI11 and PC6. Lee I-S, Lee Y-S, Park H-J, Lee H, Chae Y. Evaluation of phantom-based education system for acupuncture manipulation. PLOS One. 2015; 10 (2): e0117992. Tan T T, Wang D, Huang J K, Zhou X M, Yuan X, Liang J P, et al. Modulatory effects of acupuncture on brain networks in mild cognitive impairment patients. Neural Regen Res. 2017; 12:250-258. For LI4, a depth of 1.00 cm, and for HT7, a depth of 0.7 cm is appropriate. All values are for adults. Nishiwaki M, Takayama M, Yajima H, Nasu M, Park J, Kung J, Takakura N. A double-blind study on acupuncture sensations with Japanese style of acupuncture: comparison between penetrating and placebo needles. Evid Based Complement Alternat Med. 2018:8128147.

ST36 is located approximately 6 cm distal to the depression below the patella and approximately 2 cm lateral to the anterior ridge of the tibia. LI4 is located at the highest point of the web space between the thumb and index finger.

LI11 is located at the lateral (radial) corner of the crease of the elbow when the arm is bent at the elbow. PC6 is located at the center of the forearm (palmar side), between the tendons of the palmaris longus and the flexor carpi radialis muscles, approximately 6.7 cm proximal to the crease of the wrist. Acupuncture points are likely between 2 and 4 mm in diameter.

The depth of the acupuncture point depends on the body mass index of the person. Therefore, the depth of magnetic stimulation by the device will be adjustable. For ensuring safe operation, the device could be marketed specifically to acupuncture therapists and physical therapists who are already comfortable with needling techniques. For home use the device could be dispensed by a physical therapist after instructing the patient in its use, much as was done with TENS units for pain control. A timer would set stimulation to a preset duration, with a maximum duration of 30 minutes.

Typical stimulation parameters for electroacupuncture, in which a current is fed through an acupuncture needle, are 1 mA at 2 Hz for 20 minutes once a day. Transcranial magnetic stimulation protocols of the brain are also generally 20-30 minutes in duration. Therefore, 20-30 minutes will be modal for use of the unit.

The following references, each of which is incorporated by reference herein, can facilitate understanding of the invention:

Zhang Q, Li Y-N, Guo Y-Y, Yin C=P, Gao F, Xin X, Huo S-P, Wang X-L, Wang Q-J. Effects of preconditioning of electro-acupuncture on postoperative cognitive dysfunction in elderly: A prospective, randomized, controlled trial. Medicine. 2017; 96:26 (e7375).

Yoo S-S, Lee W, Kim H. Pulsed application of focused ultrasound to the LI4 elicits deqi sensations: pilot study. Complement Ther Med. 2014; 22:592-600.

Bertuccelli M, Ciringione L, Rubega M, Bisiacchi P, Masiero S, Del Felice A, et al. Cognitive impairment in people with previous COVID-19 infection: A scoping review. Cortex. 2022; 154:212-230.

U.S. Pat. Nos. 11,491,341; 10,398,907; 10,639,494; 7,979, 105; 6,488,617.

European patent application EP 1 614 443 A1.

Magnetic Plunger Example Embodiments

Figure 9:
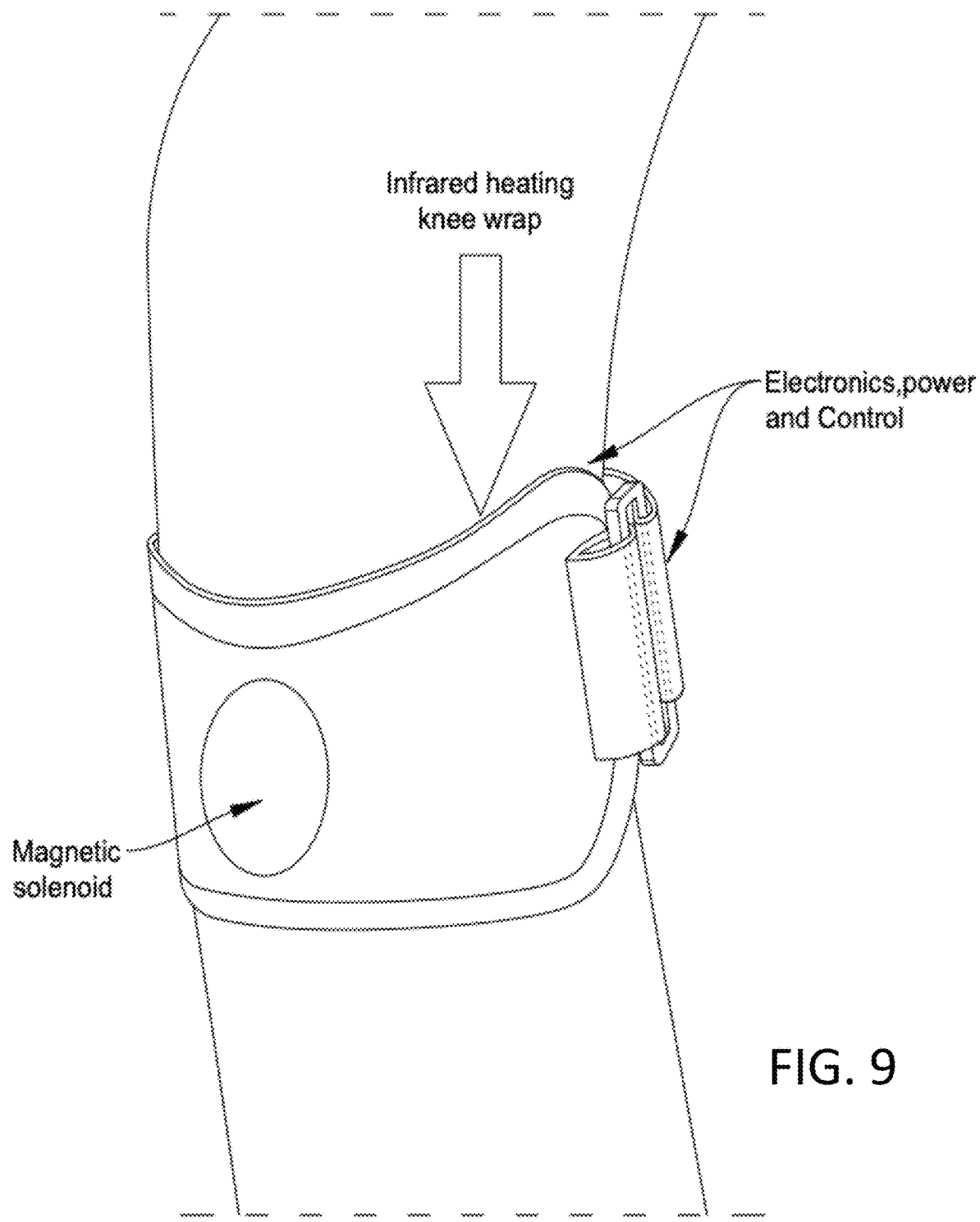
FIG. 9 is a schematic illustration of an example embodiment.

FIG. 9 is a schematic illustration of an example embodiment. A knee wrap comprising a material suitable for secure engagement with a patient's leg houses a heating system, e.g., a plurality noninvasive heating elements, and a magnetic plunger or solenoid, and suitable electronics, power, and control. The knee wrap is configured to retain the heating system and the magnetic plunger in an appropriate position relative to the desired acupoint. A suitable location of the knee brace, which is called a ST36 (acupuncture post) knee brace is right over the location of ST36 acupuncture post. In particular, the Zusanli or ST36 acupoint is located at the anterolateral lower leg, approximately 6 cm distal to the depression below the patella, approximately 2 cm lateral to the anterior ridge of the tibia, and a depth of 1-1.5 cm (see FIG. 2). This acupoint includes subcutaneous connective tissue, a portion of the proximal anterior tibialis muscle, the overlying fascia, and a nerve trunk of the deep peroneal nerve.

Figure 10:
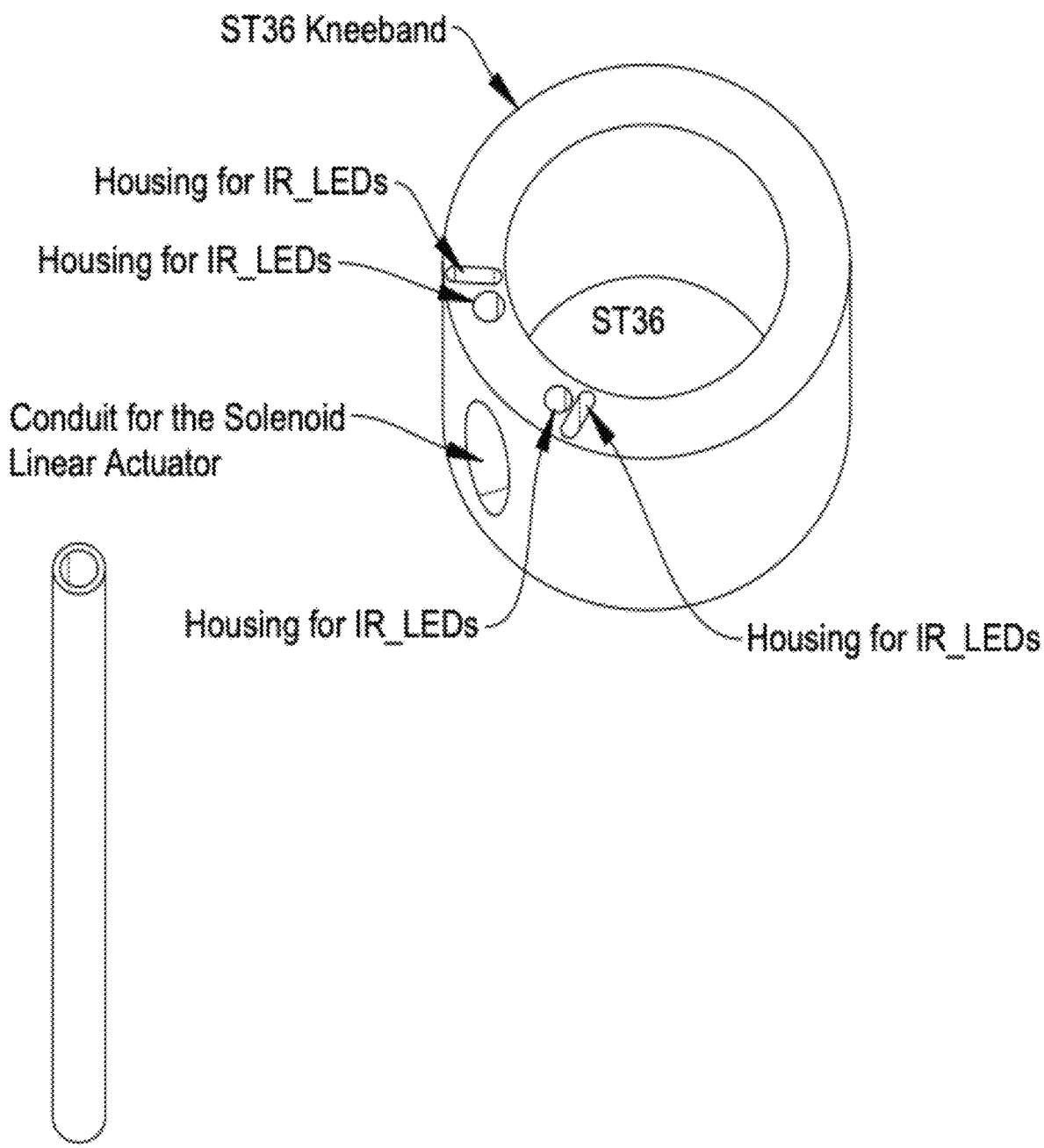
FIG. 10 is a schematic illustration of an example embodiment.

FIG. 10 is a schematic illustration of an example embodiment. Several openings in an ST36 kneeband are sized to accommodate IR LEDs for heating, and positioned such that they will be proximal the ST36 acupoint when in the kneeband is worn by a patient. A hole or conduit through the kneeband allows a magnetic plunger (shown apart from the kneeband) to translate toward and away from the patient. The varying distance of the plunger from the knee provides for a varying magnetic field strength experienced by the acupoint.

Figure 11:
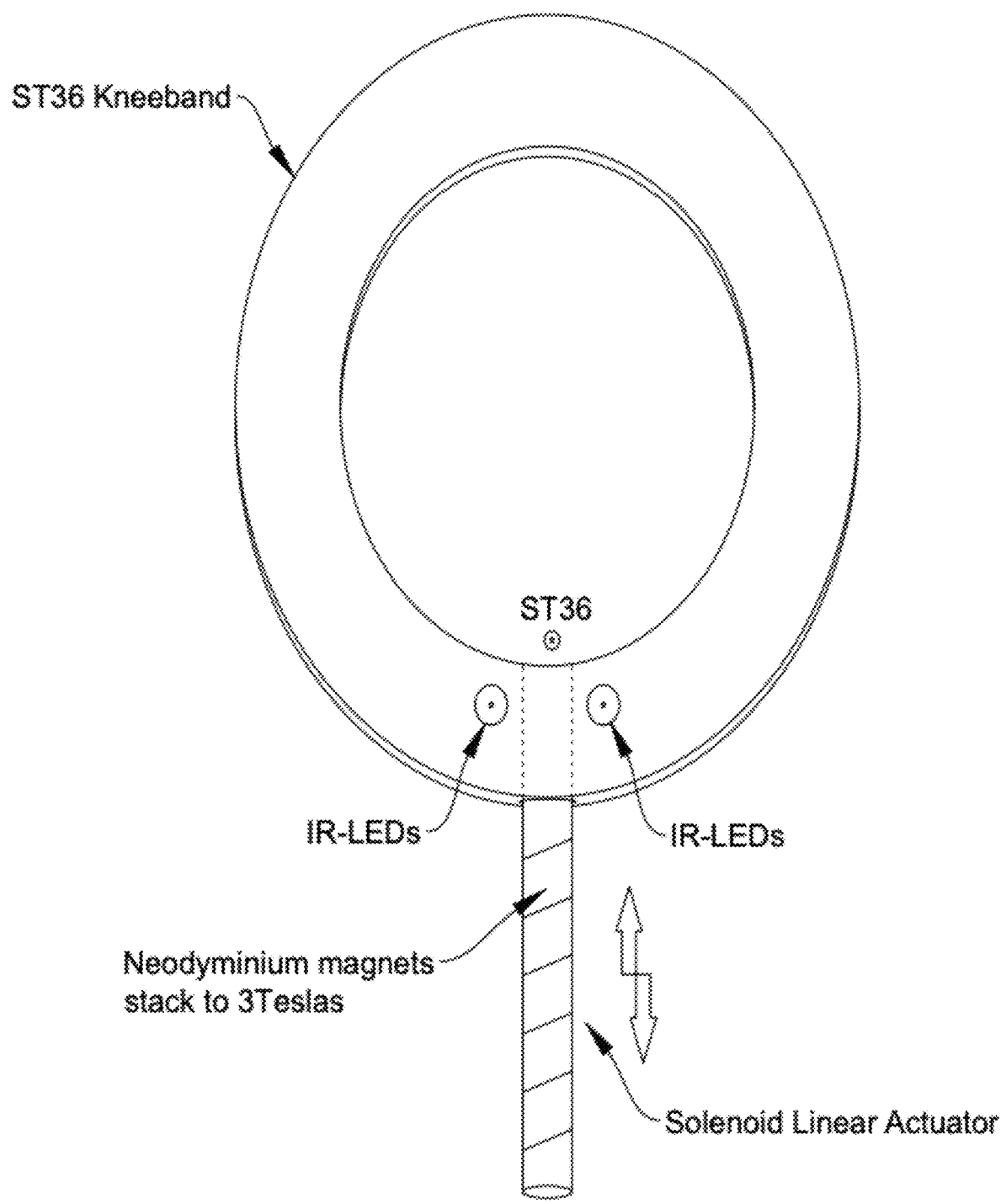
FIG. 11 is another schematic illustration of an example embodiment.

FIG. 11 is another schematic illustration of an example embodiment. The figure shows a magnetic plunger—a stack of neodymium magnets, together producing a field of up to 3 Tesla. The plunger is configured with a solenoid linear actuator that translates the plunger toward the knee (upward in the figure) and away from the knee (downward in the figure).

Figure 12:
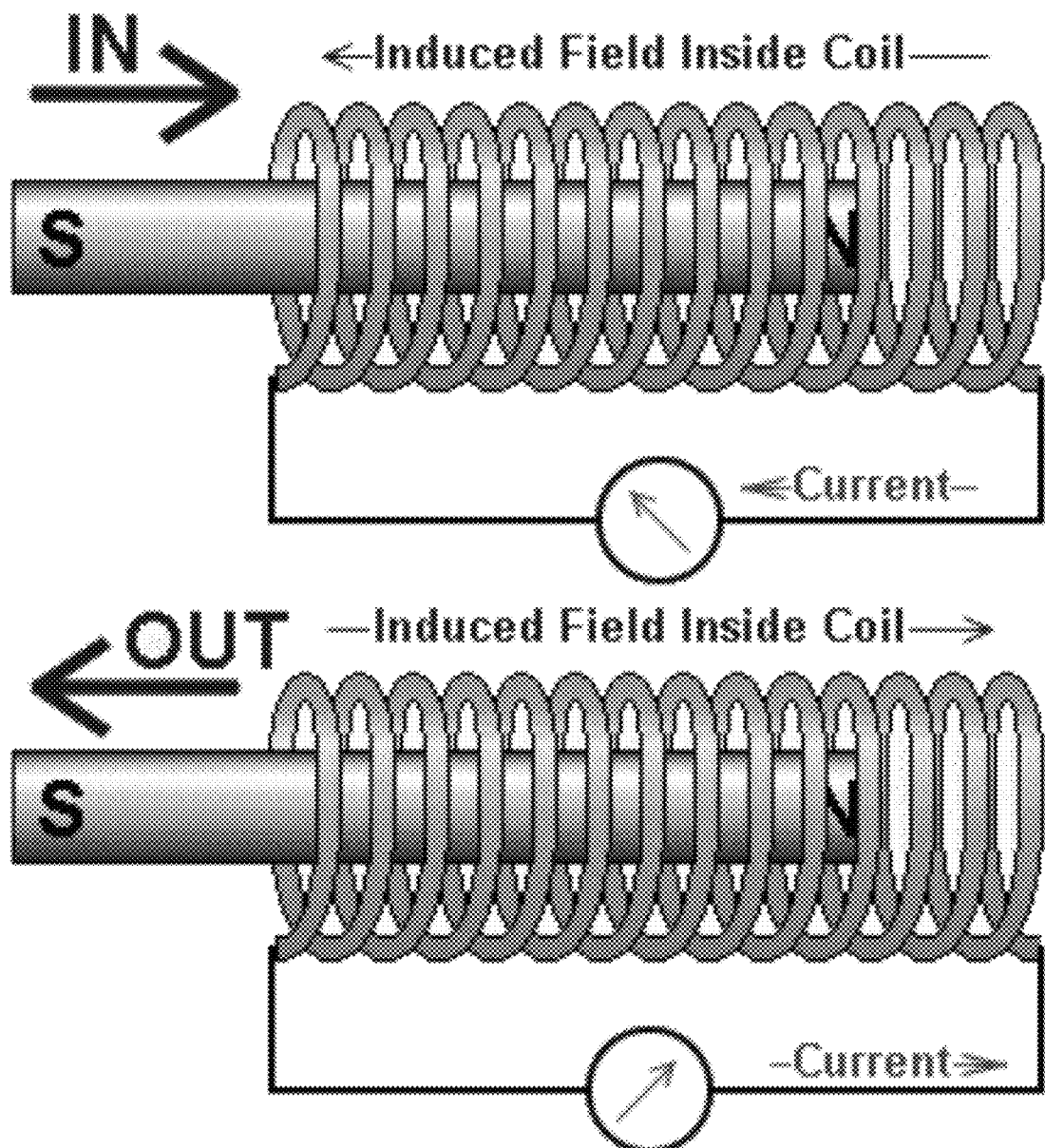
FIG. 12 is a schematic illustration of a solenoid and plunger portion of an example embodiment.

FIG. 12 is a schematic illustration of a solenoid and plunger portion of an example embodiment. The plunger is surrounded by coils that can be selectively energized. The direction of current in the coils is related to the direction of force applied to the plunger. Control of the direction and magnitude of current flow in the coils thus allows control of the positioning of the plunger relative to the acupoint. The plunger can be, for example, 5 mm in diameter. Electronics to control such solenoids are well known in the art.

Figure 13:
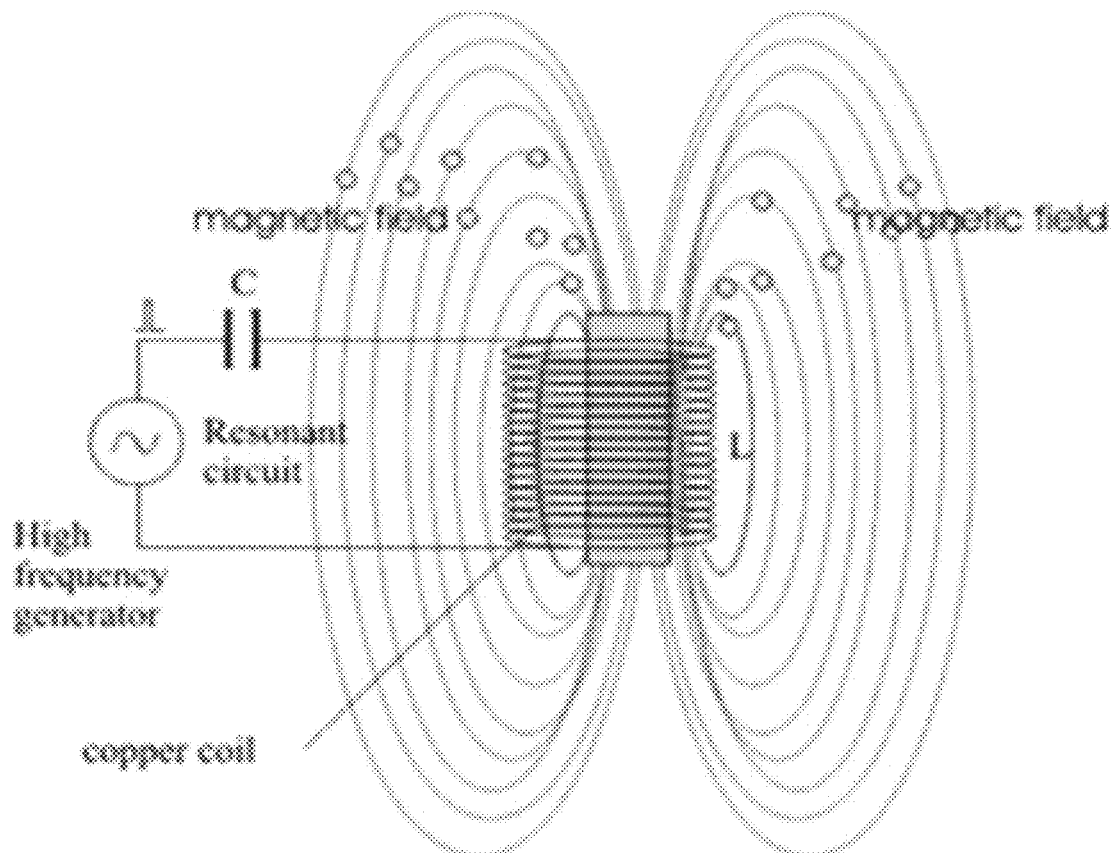
FIG. 13 is a schematic illustration of a dynamic magnetic field due to movement of the magnetic plunger towards or away from the ST36 Acupoint.
Figure 14:
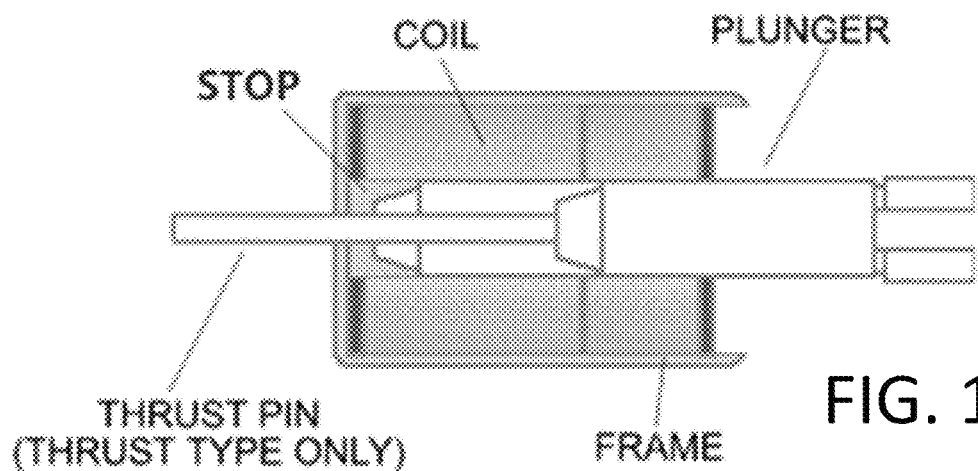
FIG. 14 is a schematic illustration of a neodymium magnetic stack linear solenoid actuator.

FIG. 13 is a schematic illustration of a dynamic magnetic field due to movement of the magnetic plunger towards or away from the ST36 Acupoint in an example embodiment like those described herein. FIG. 14 is a schematic illustration of a neodymium magnetic stack linear solenoid actuator.

Figure 15:
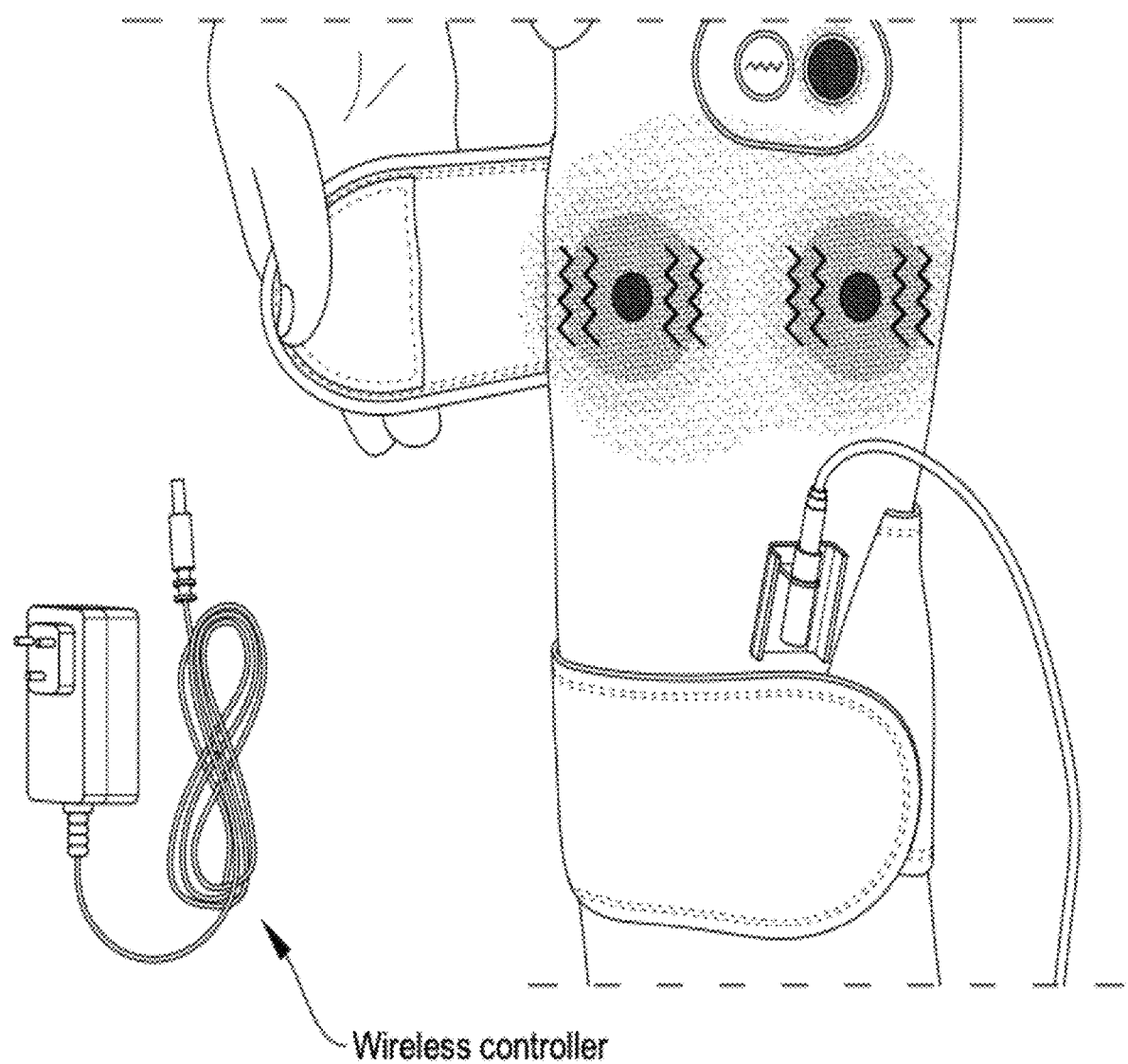
FIG. 15 is a schematic illustration of an example embodiment showing heating using the IR LEDs.

Suitable neodymium magnetics can have the following properties:
Tolerances: ¬±0.1 mm×¬±0.1 mm
Material: NdFeB, Grade N35
Plating/Coating: Ni—Cu—Ni (Nickel)
Magnetization Direction: Axial (Poles on Flat Ends)
Weight: 0.0111 oz. (0.316 g)
Pull Force, Case 1: 0.86 lbs
Pull Force, Case 2: 2.67 lbs
Surface Field: 2706 Gauss
Max Operating Temp: 176 degrees F. (80 degrees C.)
Brmax: 12,100 Gauss
BHmax: 35 MGOe FIG. 15 is a schematic illustration of an example embodiment showing heating using the IR LEDs.

Figure 16:
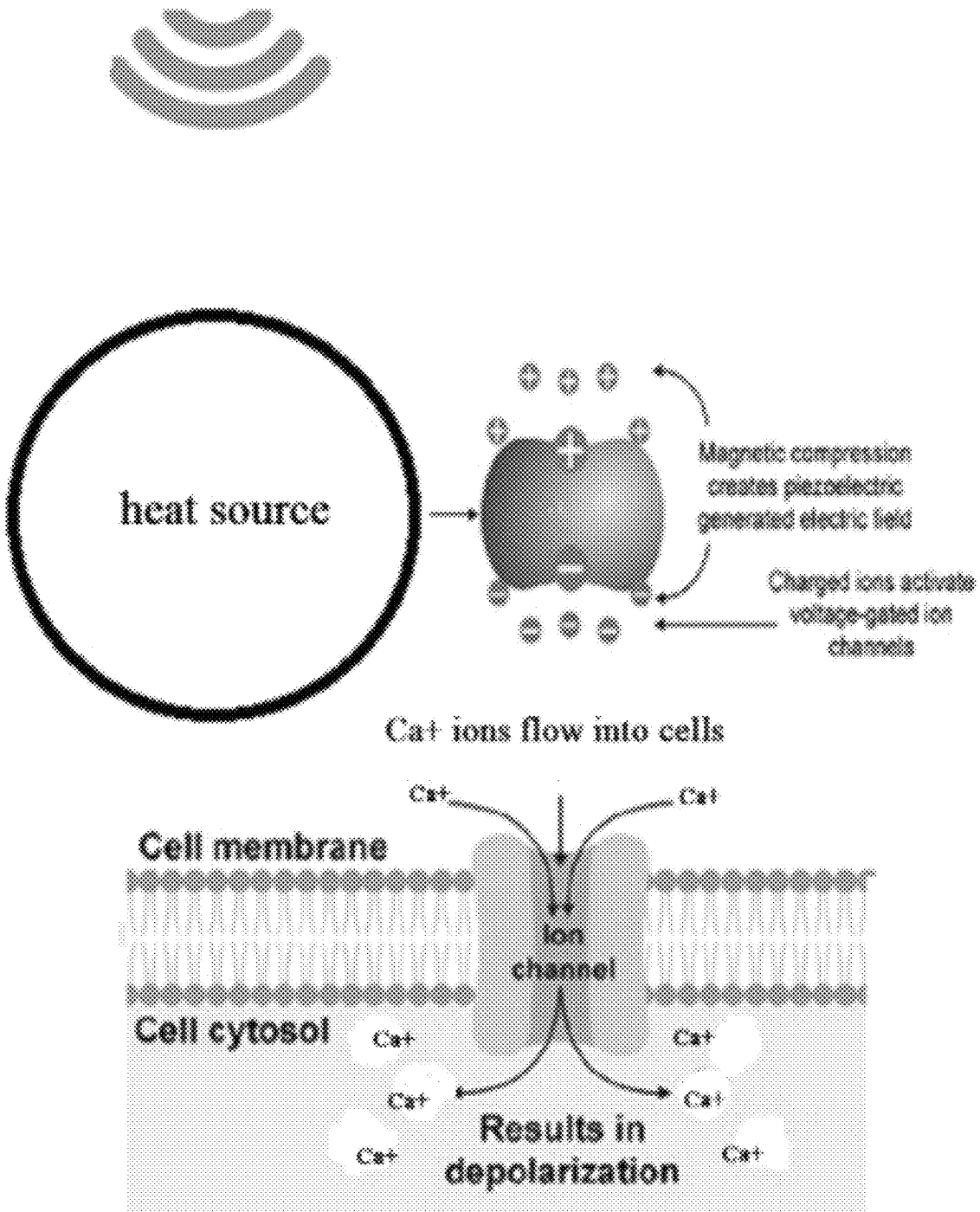
FIG. 16 is an illustration of the operation of example embodiments.
Figure 17:
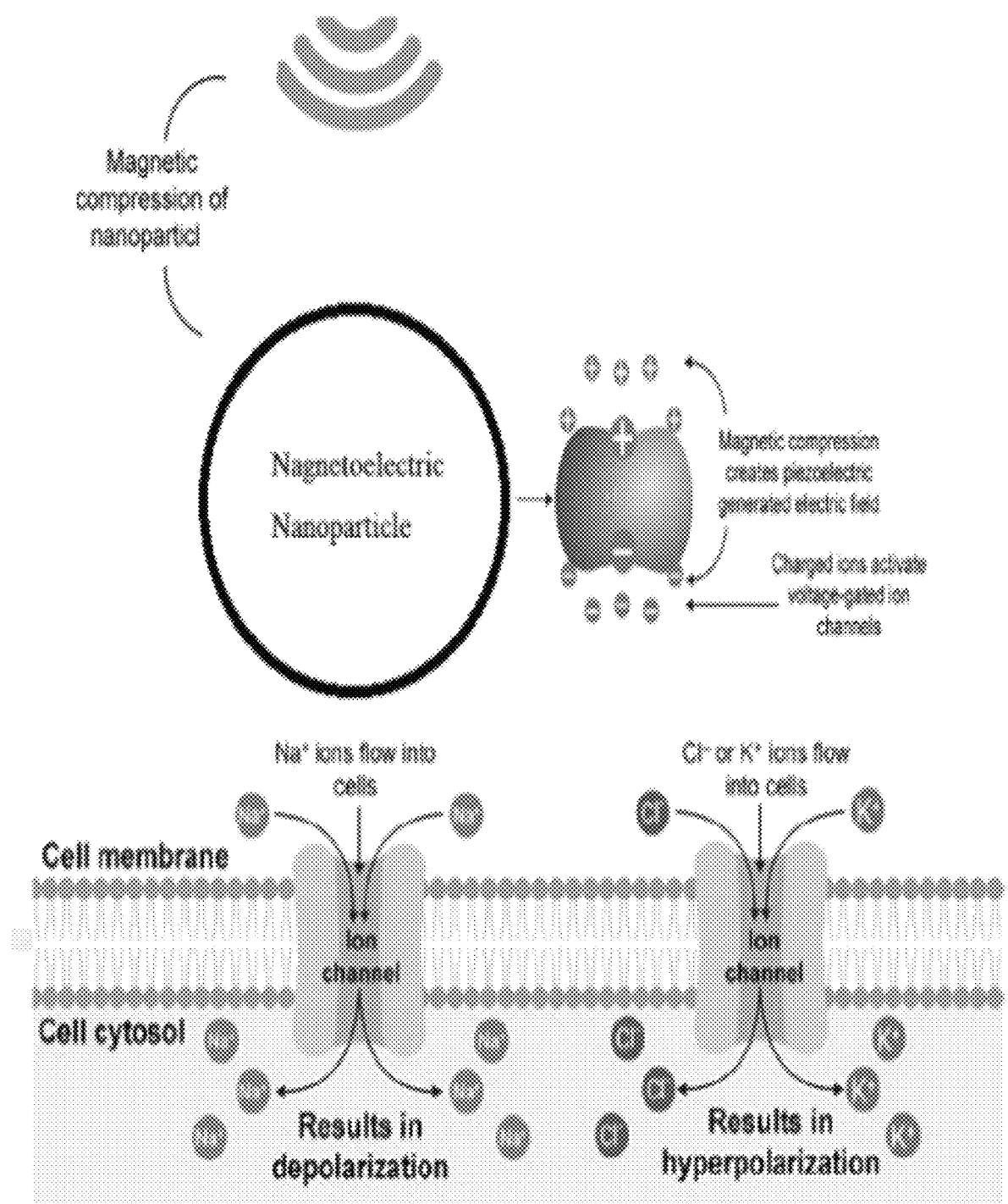
FIG. 17 is an illustration of the operation of example embodiments.

FIGS. 16 and 17 are illustrations of the operation of example embodiments.

Figure 18:
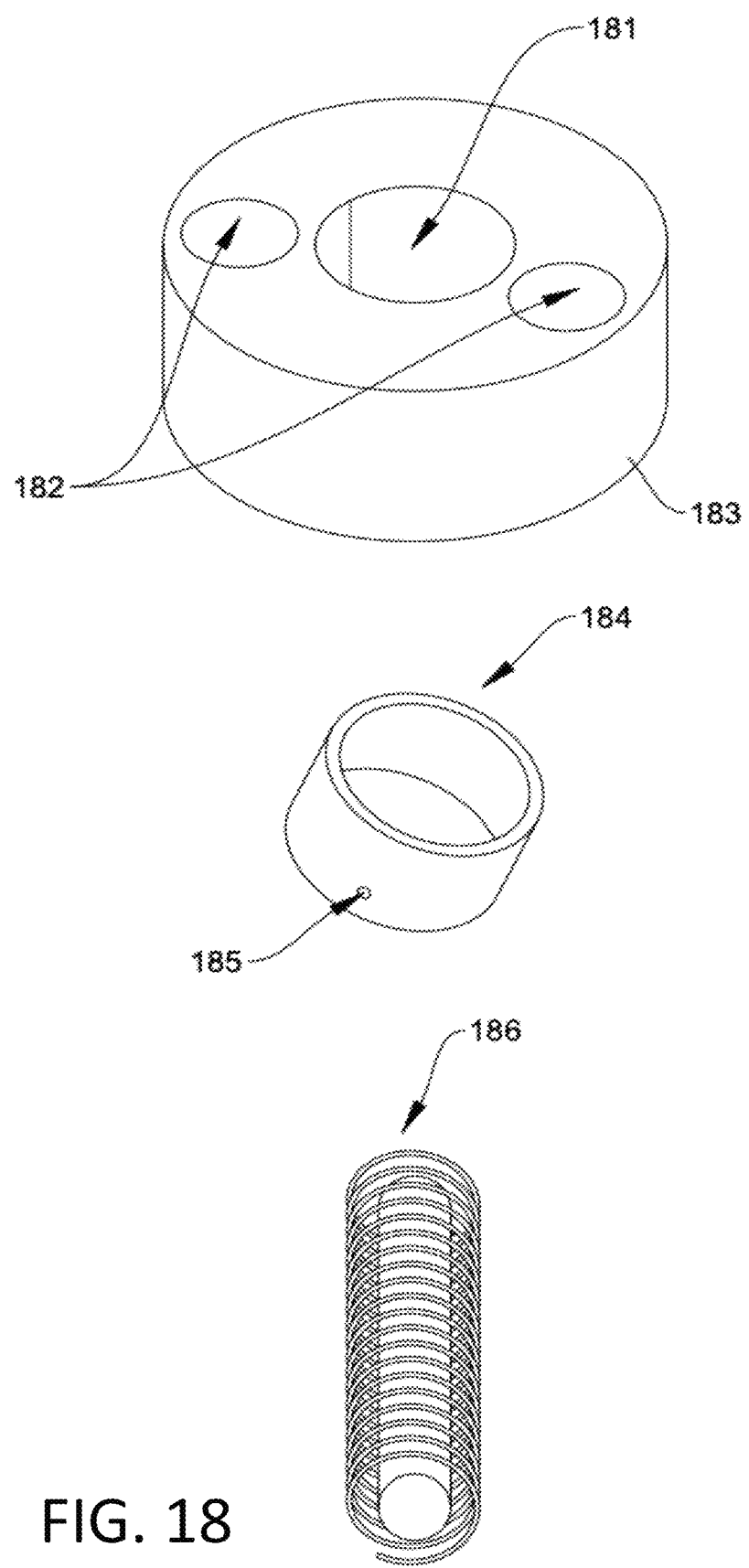
FIG. 18 is an illustration of a compact embodiment with a solenoid and timers to activate the solenoid and noninvasive heating elements over the skin periodically.

FIG. 18 is an illustration of a compact embodiment with a solenoid 186 and timers to activate the solenoid and the heating elements 182 over the skin periodically. A disk-shaped tablet 183 provides a compact embodiment that is self-contained, and can mount with a band 184 or similar apparatus for securing to the user, e.g., by placing into a hole 185 in the band. The tablet houses one or more watch batteries (e.g., Zn-Air batteries, e.g., positioned underneath the heating elements) as well as one or more timers (e.g., underneath the heating elements 182) that turn on and off periodically (e.g., every few minutes) and periodically heat associated heating elements 182 to maintain a temperature of about 44-52 degrees C. in the ST36 acupoint. The heating elements 182 can be thin film resistive heating elements, as an example. The timer(s) causes the batteries to periodically heat the thin heating elements on the skin and right on top of the ST36 acupoint to 44-52° C. This embodiment also allows the solenoid to move closer to or farther from the ST36 acupoint. As shown in the figure, a solenoid 186 can be disposed inside the cylindrical hole 181 of the tablet.

Figure 19:
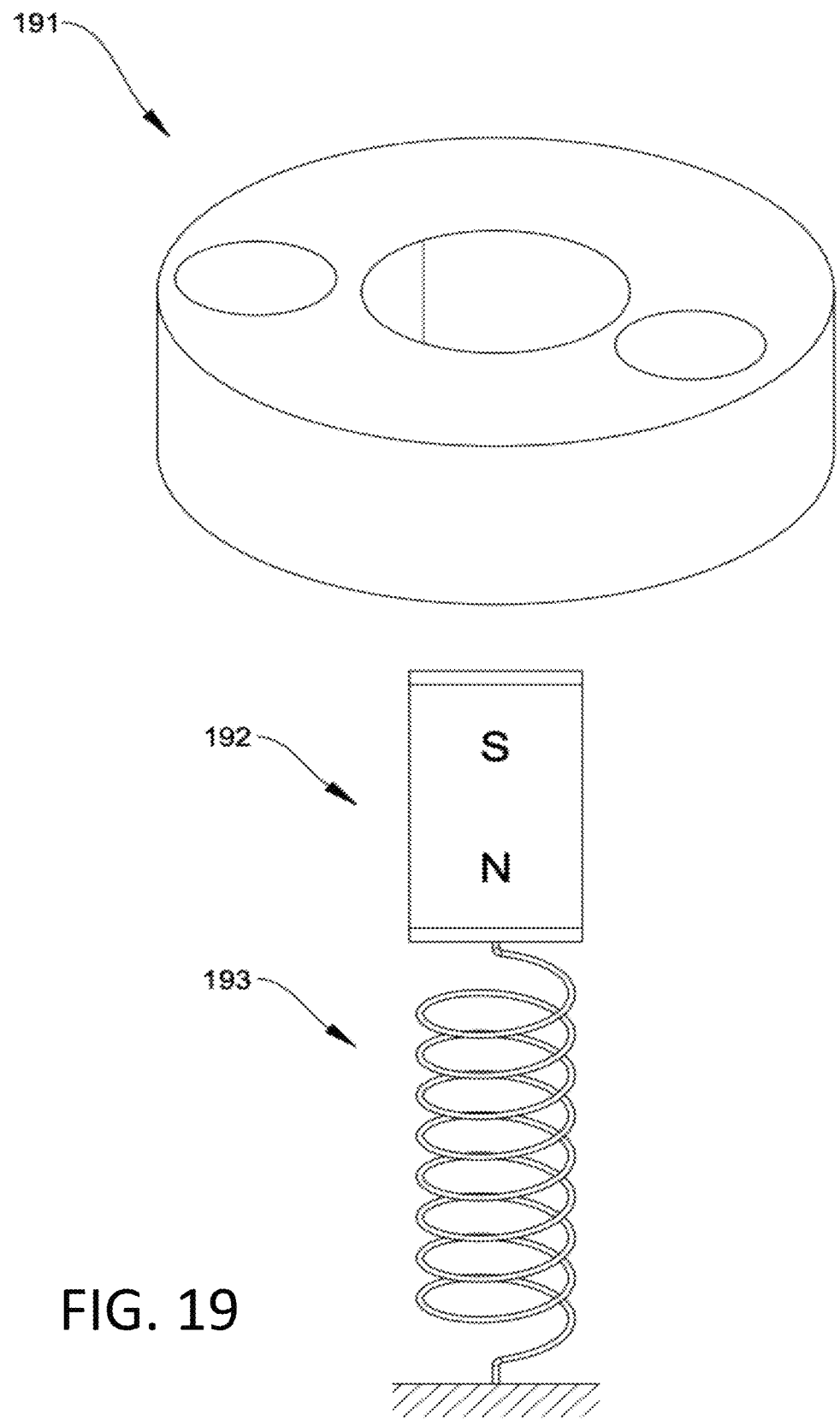
FIG. 19 is an illustration of moving a neodymium rare earth magnetic plunger close to or farther from the ST36 acupoint using a flexible oscillating helical spring.

FIG. 19 is an illustration of moving a neodymium rare earth magnetic plunger 192 being moved by a solenoid close to or farther from the ST36 acupoint using a flexible oscillating helical spring 193. A tablet 191, similar to that in FIG. 18, is provided. A neodymium-strong rare earth magnetic plunger 192 is disposed within the hole in the tablet, along with a flexible oscillating helical spring 193. A user can deform the spring and let the plunger oscillate a few times to get the magnetic field fluxes closer or farther away from ST36. Those skilled in the art will appreciate selection of appropriate springs, based on masses of the magnet and spring, length of the spring, desired force and range of motion, and desired oscillation characteristics.

The present invention has been described in connection with various example embodiments. It will be understood that the above description is merely illustrative of the applications of the principles of the present invention, the scope of which is to be determined by the claims viewed in light of the specification. Other variants and modifications of the invention will be apparent to those skilled in the art.

What is claimed is:

1. An apparatus for stimulating one or more acupuncture points, comprising: (a) a heat generator configured to apply a continuous noninvasive heating stimulation to the one or more acupuncture points; and (b) a magnetic field generator configured to contemporaneously noninvasively apply an oscillatory magnetic field stimulation to the one or more acupuncture points, where the magnetic field generator comprises a magnetic plunger configured to move between a first position at a first distance from the one or more acupuncture points and a second position at a second distance, greater than the first distance, from the one or more acupuncture points, where both the first distance and the second distance are positive distances such that skin at the one or more acupuncture points is not penetrated.

2. An apparatus for stimulating one or more acupuncture points, comprising: (a) a tablet with one or more heating elements mounted with the tablet with one or more timers configured to control the one or more heating elements such that a continuous temperature is maintained, configured to apply a continuous noninvasive heating stimulation to the one or more acupuncture points; and (b) a magnetic field generator configured to contemporaneously apply an oscillatory magnetic field stimulation to the one or more points, where the magnetic field generator comprises a magnetic plunger configured to move between a first position at a first distance from the one or more acupuncture points and a second position at a second distance, greater than the first distance, from the one or more acupuncture points, wherein the magnetic field generator is mounted with the tablet in a hole through the tablet.

3. The apparatus of claim 2, wherein the one or more heating elements further comprises one or more batteries removably mounted with the tablet and configured to provide electrical power to the one or more heating elements and the one or more timers.

4. The apparatus of claim 2, wherein the magnetic field generator comprises a solenoid with which the magnetic plunger is mounted and configured to move the magnetic plunger between a first position at a first distance from a first acupuncture point of the one or more acupuncture points and a second position at a second distance, greater than the first distance, from the first acupuncture point.

5. The apparatus of claim 2, wherein the magnetic field generator comprises a magnet mounted with a spring, where the magnet and the spring mount with the tablet within the hole through the tablet, and where oscillation of the spring moves the magnet closer to and farther from a first acupuncture point.

6. The apparatus of claim 5, wherein the magnet comprises a neodymium magnet.

7. The apparatus of claim 2, wherein the magnetic field generator comprises a solenoid with which the magnetic plunger is mounted such that operation of the solenoid moves the magnetic plunger between the first and second position.

8. The apparatus of claim 7, wherein the solenoid is configured to repeatedly move the plunger from the first position to the second position and then return the plunger to the first position, at a rate of 0.5 to 100 Hz.

9. The apparatus of claim 8, wherein the rate is 0.5 to 3 Hz.

10. The apparatus of claim 2, wherein the one or more heating elements are configured to heat tissue at the one or more points to a temperature in the range from 44 to 52 degrees C.

11. The apparatus of claim 2, wherein the magnetic field generator is configured to apply a magnetic field stimulation to the one or more acupuncture points at a strength in the range from 0.1 to 3.0 Tesla.

12. The apparatus of claim 11, wherein the one or more heating elements are configured to heat tissue at the one or more points to a temperature in the range from 44 to 52 degrees C.

13. A method of stimulating one or more acupuncture points, comprising: (a) providing an apparatus comprising: (a1) a heat generator configured to apply a continuous noninvasive heating stimulation to the one or more acupuncture points; and (a2) a magnetic field generator configured to contemporaneously apply an oscillatory magnetic field stimulation to the one or more acupuncture points, where the magnetic field generator comprises a magnetic plunger configured to move between a first position at a first distance from a first acupuncture point of the one or more acupuncture points and a second position at a second distance, greater than the first distance, from the first acupuncture point; (b) using the heat generator to heat tissue near the first acupuncture point to a temperature in the range from 44 to 52 degrees C.; and (c) moving the plunger between the first and second positions repeatedly at a rate of 0.5 to 100 Hz.

14. A method of treating a subject for a physical condition, specifically for ameliorating or preventing cognitive impairment, preventing or treating age-related cognitive decline, preventing or treating depression, post-intensive care unit syndrome, or a combination thereof, comprising stimulating one or more acupuncture points using the method of claim 13.

15. The method of claim 14, wherein the condition is one or more of the following: Alzheimer's and a neurodegenerative disease.

16. The method of claim 14, wherein the condition is one or more of the following: decline in short-term memory for verbal material; decline in verbal fluency, decline in short-term memory for visuospatial material, decline in visuospatial ability, decline in attention span, and decline in abstract reasoning.

17. The method of claim 14, wherein the condition is one or more of the following: traumatic brain injury, ischemic cerebrovascular accident, hemorrhagic cerebrovascular accident, vascular dementia, and age-related cognitive decline.

18. The method of claim 14, wherein the condition is one or more of the following: Major Depressive Disorder, Dysthymic Disorder, Adjustment Disorder with Depressed Mood, or other depressive disorder.

19. The method of claim 14, wherein the condition is post-COVID cognitive impairment, post-ICU cognitive impairment, delirium, or post-chemotherapy-induced cognitive impairment.

20. The method of claim 14, wherein the one or more acupuncture points comprise one or more of the following acupuncture points: ST36 (Zusanli), LI11 (Quchi), LI4 (Hegu), PC6 (Neiguan), and HT7 (Shenmen).

* * * * *